United States Patent
Bhattacharya et al.

(10) Patent No.: US 9,128,014 B2
(45) Date of Patent: Sep. 8, 2015

(54) HIGH THROUGHPUT AND VOLUMETRIC ERROR RESILIENT DILUTION WITH DIGITAL MICROFLUIDIC BASED LAB-ON-A-CHIP

(75) Inventors: Bhargab B. Bhattacharya, Kolkata (IN); Sarmishtha Ghoshal, Kolkata (IN); Sudip Roy, Kolkata (IN); Krishnendu Chakrabarty, Chapel Hill, NC (US)

(73) Assignee: INDIAN STATISTICAL INSTITUTE, Kolkata (IN)

(*) Notice: Subject to any disclaimer, the term of this patent is extended or adjusted under 35 U.S.C. 154(b) by 58 days.

(21) Appl. No.: 13/809,328

(22) PCT Filed: Nov. 12, 2010

(86) PCT No.: PCT/IB2010/002895
§ 371 (c)(1),
(2), (4) Date: Jan. 9, 2013

(87) PCT Pub. No.: WO2012/007786
PCT Pub. Date: Jan. 19, 2012

(65) Prior Publication Data
US 2013/0105318 A1 May 2, 2013

(30) Foreign Application Priority Data
Jul. 15, 2010 (IN) .............................. 769/KOL/2010

(51) Int. Cl.
*G01N 1/38* (2006.01)
*B01F 13/00* (2006.01)
(Continued)

(52) U.S. Cl.
CPC .............. *G01N 1/38* (2013.01); *B01F 13/0071* (2013.01); *B01F 13/0076* (2013.01); *B01F 15/0404* (2013.01); *B01L 3/502784* (2013.01); *B01F 2003/0896* (2013.01)

(58) Field of Classification Search
CPC .... B01L 3/502769–3/502784; G01N 27/4473; G01N 27/44791; G01N 1/38; G01N 2001/386; B01F 13/0069; B01F 13/0072
See application file for complete search history.

(56) References Cited

U.S. PATENT DOCUMENTS 6,565,727 B1 5/2003 Shenderov
6,911,132 B2 6/2005 Pamula et al.
(Continued)

FOREIGN PATENT DOCUMENTS

JP 2006-500596 1/2006
WO WO 2010/077859 7/2010

OTHER PUBLICATIONS

M. Pollack, "5.2 Capacitive Droplet Detection", Electrowetting-based microactuation of droplets for digital microfluidics, Ph.D. Dissertation, Feb. 2001, Duke University, pp. 122-128.*
(Continued)

*Primary Examiner* — J. Christopher Ball
(74) *Attorney, Agent, or Firm* — Workman Nydegger

(57) ABSTRACT

Systems and methods are provided for producing fluids with desired concentration factors from the given supply of any two concentration factors, one greater than the target CF and one less than the target CF, of the same fluid. According to one embodiment, a method is provided that stores intermediate waste droplets from a sequence of mix and split steps and repeats certain steps of the sequence using the stored intermediate waste droplets. Such a method may produce additional target CF droplets faster than repeating the entire sequence. In another embodiment, a method of volumetric error resilient target CF droplet generation has been described, and includes reusing the stored intermediate waste droplets and involves a collection of capacitive sensing circuits associated with some electrode platforms.

21 Claims, 16 Drawing Sheets

(51) Int. Cl.
*B01F 15/04* (2006.01)
*B01L 3/00* (2006.01)
*B01F 3/08* (2006.01)

(56) References Cited

U.S. PATENT DOCUMENTS

| | | | |
|---|---|---|---|
| 7,569,129 | B2 | 8/2009 | Pamula et al. |
| 2004/0031688 | A1 | 2/2004 | Shenderov |
| 2004/0055891 | A1 | 3/2004 | Pamula et al. |
| 2013/0105319 | A1 | 5/2013 | Bhattacharya et al. |
| 2013/0115703 | A1 | 5/2013 | Bhattacharya et al. |

OTHER PUBLICATIONS

H. Ren, "4. Digital On-Chip Dilution", Electro-wetting based sample preparation: An initial study for droplet transportation, creation and on-chip digital dilution, Ph.D. Dissertation, Mar. 2004, Duke University, pp. 71-90.*
Ren, et al. "Automated on-chip droplet dispensing with volume control by electro-wetting actuation and capacitance metering" Sensors and Actuators B, vol. 98, No. 1, Mar. 2004, p. 319-327.*
Fair, "Digital microfluidics: is a true lab-on-a-chip possible?," Microfluidics and Nanofluidics, vol. 3, Jun. 2007, pp. 245-281.
Thies, "Programable Microfluidics", [retrieved on Mar. 2, 2011]. Retrieved from Internet; Inthttp://replay.waybackmachine.org/20090620134748/http://groups.csail.mit.edu/cag/bios; published on Jun. 20, 2009 as per Wayback Engine.
Thies, et al. "Abstraction layers for scalable microfluidic biocomputing," Natural Computing, vol. 7, Jun. 2008, pp. 255-275.
International Search Report and Written Opinion from International Application No. PCT/IB2010/002911 dated Mar. 9, 2011.
International Search Report and Written Opinion from International Application No. PCT/IB2010/002899 dated Feb. 22, 2011.
International Search Report and Written Opinion from International Application No. PCT/IB2010/002895 dated Apr. 5, 2011.
Zheng, et al., "A Microfluidic Approach for Screening Submicroliter volumes against Multiple Reagents by Using Preformed Arrays of Nanoliter Plugs in a Three-Phase Liquid/Liquid/Gas Flow," Angewandte Chemie (International ed. in English), vol. 44, Apr. 2005, pp. 2520-2523.
Xu, et al, "Automated, Accurate, and Inexpensive Solution-Preparation on a Digital Microfluidic Biochip". Biomedical Circuits and Systems Conference, 2008. BioCAS 2008. pp. 301-304.
Yuh, et al, "Placement of Digital Microfluidic Biochips Using the T-tree Formulation" Design Automation Conference, 2006 43rd ACM pp. 931-934.
Ding, Jie., et al., "Scheduling of Microfluidic Operations for Reconfigurable Two-dimensional Electrowetting Arrays," IEEE Transactions on Computer-Aided Design of Integrated Circuits and Systems, vol. 20,No. 12, pp. 1463-1468 (Dec. 2001).
Fair, R.B., et al., "Electrowetting-based On-chip Sample Processing for Integrated Microfluidics," IEEE IEDM'03 Technical Digest, pp. 32.5.1-32.5.4 (Dec. 2003).
Fair, R.B., et al., "Integrated Chemical/Biochemical Sample Collection, Pre-Concentration, and Analysis on a Digital Microfluidic," in Proceedings of the SPIE Conference on Lab-on-a-Chip: Platforms, Devices, and Applications, vol. 5591, pp. 113-124 (2004).
Fouillet, Y., et al ., "Digital microfluidic design and optimization of classic and new fluidic functions for lab on a chip systems," Microfluidics and Nanofluidics, vol. 4, No. 3, pp. 159-165 (Mar. 1, 2008).
Griffith, E., and Akella, S., "Coordinating Multiple Droplets in Planar Array Digital Microfluidics System," Algorithmic Foundations of Robotics, vol. 17, pp. 219-234 (Oct. 12, 2005).
Griffith, E.J. et al., "Performance Characterization of a Reconfigurable Planar-Array Digital Microfluidic System,"IEEE TCAD, vol. 25, Issue 2, pp. 340-352 (Feb. 2006).
Mitra, D., et al., "Accelerated Functional Testing of Digital Microfluidic Biochips," in Proceedings of the 17th Asian Test Symposium (ATS 2008), pp. 295-300 (Nov. 24-27, 2008).
Paik, P., et al., "Electrowetting-based Droplet Mixers for Microfluidic Systems," Lab-on-a-Chip, vol. 3, pp. 28-33 (Feb. 3, 2003).
Paik, P., et al., "Rapid Droplet Mixers for Digital Microfluidic Systems," Lab-on-a-Chip, vol. 3, pp. 253-259 (Sep. 12, 2003).
Ren, H. et al., "Design and Testing of an Interpolating Mixing Architecture for Electrowetting-Based Droplet-On-Chip Chemical Dilution," 12th International Conference on TRANSDUCERS, Solid-State Sensors, Actuators and Microsystems, vol. 1, pp. 619-622 (Jun. 8-12, 2003).
Srinivasan, V., et al.,"An Integrated Digital Microfluidic Lab-on-a-Chip for Clinical Diagnostics on Human Physiological Fluids," Lab-on-a-Chip, vol. 4, No. 4, pp. 310-315, (2004).
Urbanski, J.P., et al., "Digital Microfluidics using Soft Lithography," Lab Chip, vol. 6, No. 1, pp. 96-104 (2006).
Xu, T., and Chakrabarty, K., Functional Testing of Digital Microfluidic biochips, in Proceedings of the IEEE International Test Conference (ITC 2007), pp. 1-10 (Oct. 21-26, 2007).

* cited by examiner

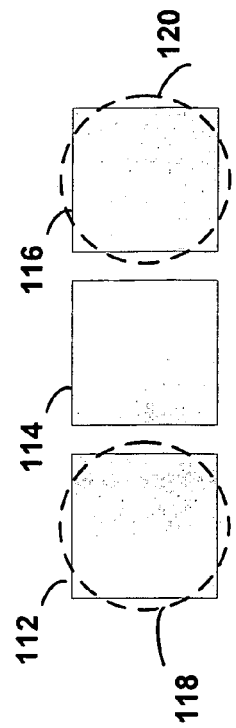
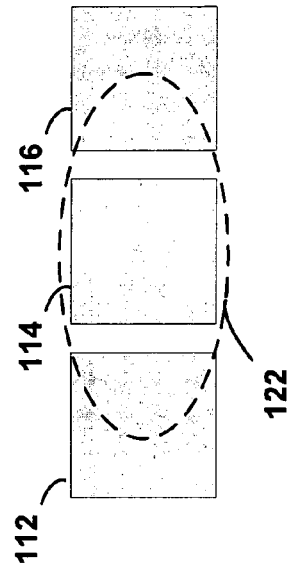
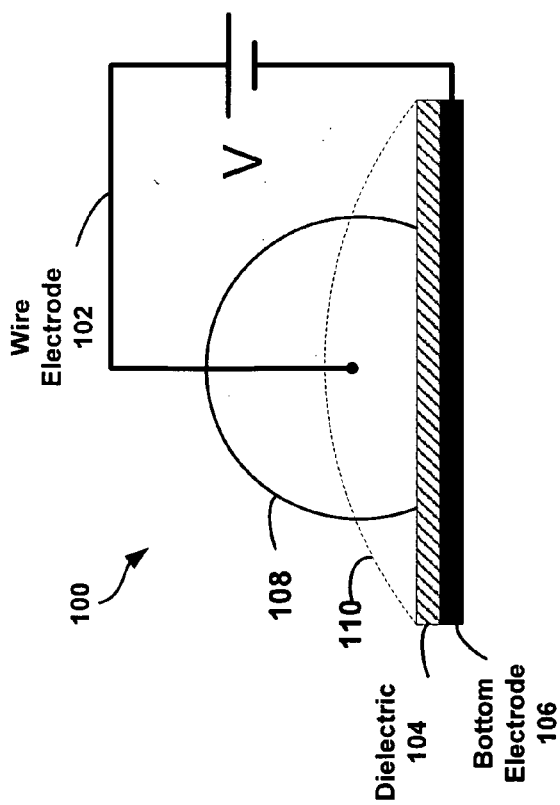
FIG. 1B
FIG. 1C
FIG. 1A

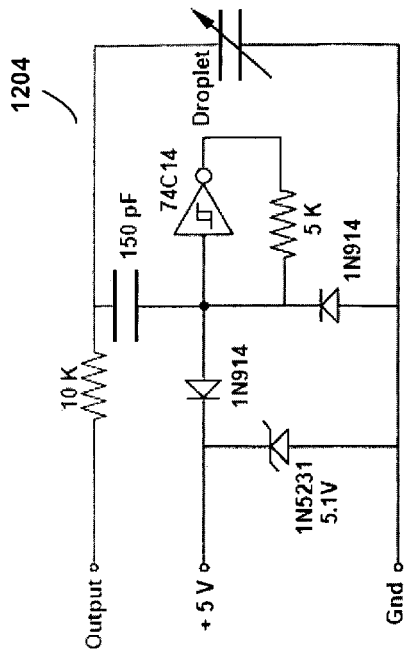
FIG. 12A
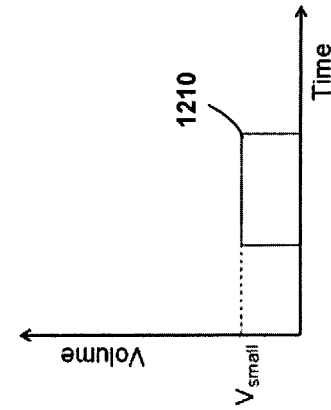
FIG. 12B
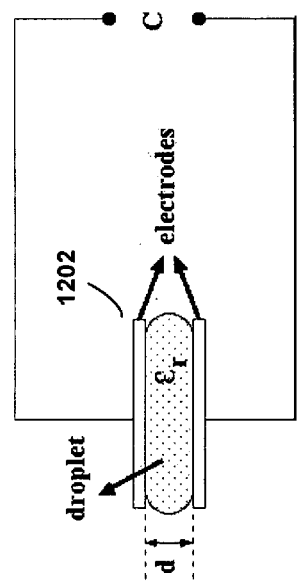
FIG. 12C
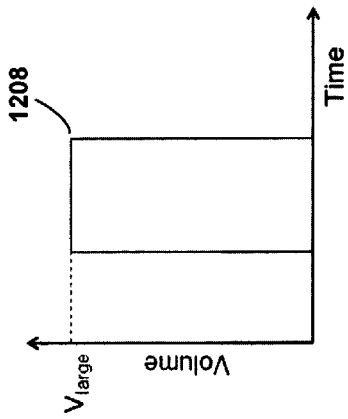
FIG. 12D
FIG. 12E

HIGH THROUGHPUT AND VOLUMETRIC ERROR RESILIENT DILUTION WITH DIGITAL MICROFLUIDIC BASED LAB-ON-A-CHIP

CROSS-REFERENCE TO RELATED APPLICATION

This application is a U.S. National phase filing under 35 U.S.C. §371 of PCT International Application No. PCT/IB2010/002895 filed Nov. 12, 2010, which claims priority under 35 U.S.C. §119(d) to a corresponding patent application filed in India and having application number 769/KOL/2010, filed on Jul. 15, 2010, the entire contents of which are herein incorporated by reference.

TECHNICAL FIELD

This application relates generally to dilution algorithms designed for digital microfluidic (DMF) biochips.

BACKGROUND

To meet the challenge of rising costs of laboratory diagnostics associated with prevalent diseases, such as cardiovascular disease, cancer, diabetes, HIV, etc., a new technology is emerging called "Lab-on-a-Chip (LOC)." LOC implements one or more biochemical laboratory protocols or assays on a small chip (e.g., one of a few square centimeters in area). Compared with traditional bench-top procedures, these biochips offer many advantages, namely low sample and reagent consumption, less likelihood of error due to minimal human intervention, high throughput and high sensitivity.

One example biochip, called a "digital microfluidic (DMF) biochip", is designed to integrate assay operations such as detection, as well as sample pre-treatment and sample preparation on one chip. Front-end diagnostic functions, such as dilution of a sample, can be carried out on-chip or by pre-processing during sample preparation outside the chip. Off-chip sample processing and sample preparation may pose a significant hindrance to the overall biochemical assay completion time, due to long lead times that may be required for laboratory processes. Therefore, it may be desired that for fast and high throughput applications, sample pre-processing steps, such as sample dilution, be automated on-chip, i.e., integrated and self-contained on the biochip itself.

One challenge associated with using digital microfluidic biochips for diluting samples/reagents is to use dilution schemes that both minimize waste and require a relatively small number of dilution steps to achieve the desired target concentration.

SUMMARY

In accordance with one example embodiment, a method for producing target concentration factor (CF) droplets on an arrangement of electrowetting-on-dielectric (EWOD) platforms is provided. The method includes a sequence of mixing steps, in which each mixing step includes mixing two fluid droplets having any two different CFs together to produce a resultant mixture having a resultant CF in between the two supplied CFs and splitting the resultant mixture into a first resultant droplet and a second resultant droplet. When the resultant mixture produced in the mixing step has a resultant CF not substantially equal to the target CF, the method further includes mixing the first resultant droplet with a droplet of one of two sample fluids in the next mixing step. The method further includes at least one additional mixing step, in which a droplet of one of two sample fluids is mixed with a second resultant droplet split from a resultant mixture produced in a preceding mixing step to produce a given resultant mixture having a CF substantially equal to a CF of a resultant mixture produced in one of the sequence of mixing steps.

In another example embodiment, software instructions are provided that determine a sequence of mix steps that produce two droplets having a target CF. Each determined mix step includes mixing two fluid droplets having any two different CFs together to produce a resultant mixture having a resultant CF in between the two supplied CFs and splitting the resultant mixture into a first resultant droplet and a second resultant droplet. When the CF of the resultant mixture produced in each mixing step is not substantially equal to the target CF, the first resultant droplet split in the given mixing step is mixed with a droplet of one of two sample fluids in the next mixing step of the sequence. The instructions further include determining, based on a desired number of target droplets, at which particular mixing step in the sequence of mixing steps to begin storing the produced second resultant droplets so as to use them in one or more additional mixing steps to produce additional target droplets.

In a further example embodiment, a method for preparing to mix fluid samples on a DMF biochip is provided. The method includes transporting a droplet from a sample reservoir to a first capacitive sensing circuit associated electrode and determining whether a first reading is within a threshold range of values. When the first reading is within the threshold range of values, then the method further includes transporting the droplet from the first capacitive sensing circuit associated electrode to a mixing module, and when the first reading is not within the threshold range of values, the method further includes, not transporting the droplet from the first capacitive sensing circuit associated electrode to the mixing module. The method additionally includes transporting a second droplet from a second sample reservoir to a second capacitive sensing circuit associated electrode and determining whether a second reading, which results from the second capacitive sensing circuit associated electrode holding the second droplet, is within a second threshold range of values.

In a still further example embodiment, a method for mixing and splitting droplets on a DMF biochip is provided. The method includes mixing two droplets together at a mixing module and splitting the resultant mixture into two resultant droplets, transporting one of the two resultant droplets to a first capacitive sensing circuit associated electrode and transporting the other of the two resultant droplets to a second capacitive sensing circuit associated electrode, and calculating a difference between readings produced from the first and second capacitive sensing circuits.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1A is an example of a DMF-based electrode platform.

FIG. 1B is an example 1×3 array of DMF-based electrode platforms with 2 separate droplets.

FIG. 1C is an example 1×3 array of DMF-based electrode platforms with 2 droplets mixed into one large droplet.

FIG. 12A is an example of parallel plate electrodes used as a capacitor attached with the capacitive sensing circuit.

FIG. 12B is an example circuitry that may be integrated with a capacitive sensing circuit associated electrode.

FIGS. 12C-E are example voltage waveforms that are indicative of differing droplet volumes.

DETAILED DESCRIPTION

Figure 2A:
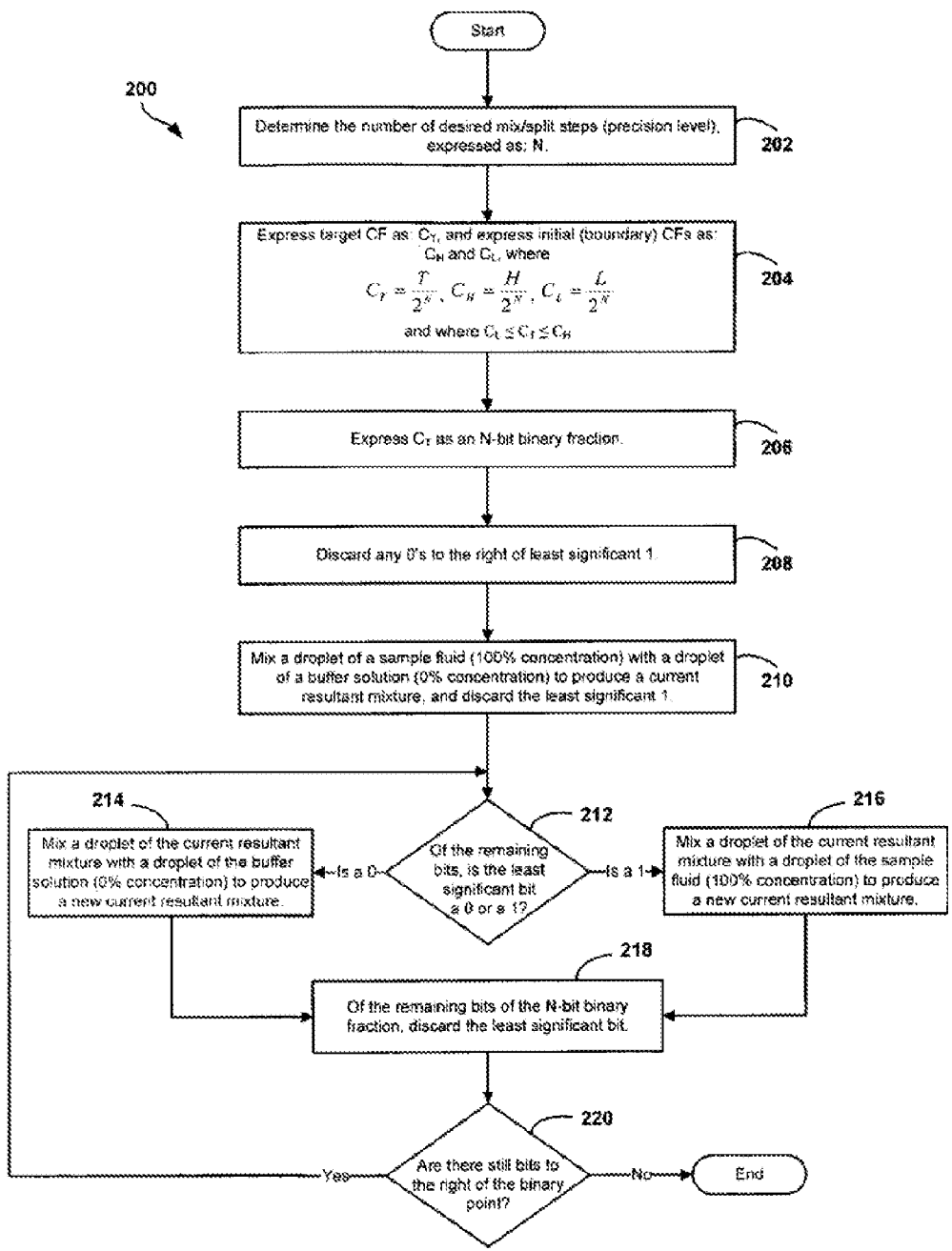
FIG. 2A is a flow chart illustrating an example algorithm for determining a sequence of mix steps used to produce a fluid droplet having a target concentration factor from the supply of sample fluid (100% concentration) and buffer solution (0% concentration).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Digital microfluidic (DMF) biochips designed to perform dilution steps may utilize electrowetting-on-dielectric (EWOD) technology. EWOD technology revolves around changing the wettability of liquids on a dielectric surface by varying the electric potential through the liquid. By way of example, FIG. 1 illustrates a droplet resting on an example EWOD electrode 100 (referred to herein as a "platform"). A relatively low electric potential applied via a wire electrode 102 and a bottom electrode 106 may cause the droplet to form a rounded shape illustrated by the solid curve 108. A relatively high electric potential applied via the wire electrode 102 and the bottom electrode 106 may cause the droplet to flatten out in the manner illustrated by the dashed curve 110. DMF-based electrode platforms, such as the one illustrated in FIG. 1, may be adjacently positioned, such that the application and de-application of electric potential to the platforms may cause a droplet to move from platform to platform. Further, the platforms may be positioned on the chip in such a way that the mixing of two or more droplets is carried out by causing the droplets to combine across one or more platforms. In addition to EWOD technology, other methods for carrying out mixing and splitting steps on a droplet-based biochip may exist as well, such as utilizing surface acoustic waves, or optoelectrowetting.

In an example of a DMF-based biochip, dielectric 104 and bottom electrode 106 may be encapsulated in a boro-aluminosilicate glass substrate (not shown in FIG. 1A). A chromium layer (e.g., of about 5 nm) and a gold layer (e.g., of about 100 nm) may be deposited onto the glass substrate and patterned by standard photolithography and wet etching. The bottom electrode may be formed of indium-tin oxide. Dielectric layer 104 may be formed of Parylene C and patterned using photolithography. An additional layer (not shown in FIG. 1A) may be added to the dielectric 104 to make the surface hydrophobic (e.g., a 0.5% Teflon AF 1060 layer of about 30 nm thickness). In some embodiments, the wire electrode 102 may take the form of a plate electrode encapsulated in a glass substrate, similar to the bottom electrode 106.

Example droplet volumes that platforms might hold with proper functionality by EWOD technique may be on the order of about 1-2 mL, though other volumes are possible as well, depending on the size of the platform. In some DMF biochips, it may not be possible to control the volume of fluid contained on a single platform. Therefore, the smallest volume of fluid that can be mixed in a mix step may be a droplet from one platform mixed with a droplet from an adjacent platform. A "unit-volume" may thus refer to the volume of a droplet able to be contained on one platform of a particular DMF biochip. Biochips may have different platform sizes depending on the overall size of the chip. Accordingly, different biochips may be associated with different unit-volumes, and may be chosen or designed as such depending on the application.

A particular DMF biochip may include an array of platforms such as any of the example 1×3 array of platforms illustrated in FIG. 1B and FIG. 1C. FIG. 1B illustrates platforms 112, 114, and 116, with platforms 112 and 116 holding respective droplets 118 and 120. Note that a platform may be considered as "holding" or "containing" a droplet if a substantial portion of the droplet resides on the platform, depending on an application of the platform, for example. Some portions of a droplet may need to be extended beyond the physical dimensions of a platform and overlap with the adjacent platforms, depending on the volume of the droplet, in order to enable the EWOD technique for droplet actuation.

An application of voltage to platform 114 and a de-application of voltage to platforms 112 and 116 may cause the droplets 118 and 120 to be attracted to platform 114. This combination of droplets 122 across platforms is illustrated in FIG. 1C. The combination or resultant droplet 122 then has a volume of about twice the volume of individual droplets 118 or 120. A re-application of voltage to platforms 112 and 116 and a de-application of voltage to platform 114 can split the combination droplet 122 and result in the configuration illustrated in FIG. 1B.

A sequence of voltages applied to an array of platforms that cause droplets to move about the array can be referred to as an actuation sequence. The actuation sequence may be expressed as a bit pattern, with a 1 representing an application of voltage, and a 0 representing a de-application of voltage. For example, an actuation sequence that results in the mixture of droplets 118 and 120 across platforms 112, 114, and 116 (shown in FIGS. 1B and 1C) is illustrated in Table 1.

TABLE 1

| Time Step | Platform 112 | Platform 114 | Platform 116 |
|---|---|---|---|
| 0 | 1 | 0 | 1 |
| 1 | 0 | 1 | 0 |
| 2 | 1 | 0 | 1 |

At time step 0, platforms 112 and 116 are driven high while 114 is driven low, thus confining droplets 118 and 120 to respective platforms 112 and 116. At time step 1, platforms 112 and 116 are driven low while platform 114 is driven high. Both droplets are thus attracted to platform 114 and consequently mix together. Finally, at time step 2, platforms 112 and 116 are again driven high while platform 114 is driven low. This applies a splitting force to the resultant droplet 122, thus dividing the droplet into two substantially equal volume droplets and containing them on platforms 112 and 116 respectively.

A DMF biochip may be used to carry out the steps of an algorithm that solves a dilution problem. A dilution problem can be stated as: given a raw sample/reagent fluid (with 100% concentration) and a neutral buffer solution (with 0% concentration), determine a sequence of one-to-one (1:1) mixing and splitting steps for obtaining a desired concentration factor (CF) of the sample. CF is usually expressed as a percentage (e.g., 23%) or a fraction (e.g., $23/100$) and can be thought of as a ratio of a volume of a raw sample to the final volume of the diluted sample after mixing with a buffer solution. An example reagent solution with CF of 100% could be a volume of saturated salt water solution, while an example buffer solution with CF of 0% could be a volume of distilled water.

In large-scale dilution applications, it may be desirable to complete the dilution application relatively quickly. Therefore, when the dilution steps are designed to be carried out on a microfluidic biochip, they may be designed such that the sequence has a relatively small number of mix/split steps. Additionally, biochips may be on the order of a few square centimeters in size and so a sequence of mix/split steps that requires no storage units (i.e., no extra area for extra storage platforms) may be desired as well.

One such example algorithm for determining and carrying out a sequence of mix/split steps that requires no storage and may be carried out relatively quickly, is a bit scanning algorithm illustrated by the flow chart 200 in FIG. 2A. The bit scanning algorithm is applicable to instances where a supplied reagent fluid (or raw sample) has a CF of 100% and a buffer solution has a CF of 0%.

The flow 200 begins at step 202 where the desired number of mix/split steps, N, is determined. After N (or less) mix/split steps, the algorithm produces a resultant solution having a CF equal to the target CF within an error in concentration factor of about $\pm 1/2^N$. Therefore, N can be thought of as a precision level, since the larger N is (the more mix/split steps allowed), the more precise the target concentration can be.

In the next step 204, the target CF and initial (boundary) CFs are each expressed as rational numbers with denominators of $2^N$, such as:

$$C_T = \frac{T}{2^N}, C_H = \frac{H}{2^N}, C_L = \frac{L}{2^N}$$

where N is a whole number. The numerator of the target CF can be expressed as T, where T is a whole number and where $0 < T < 2^N$ (i.e., $C_L < C_T < C_H$).

Continuing at step 206, the target CF is expressed as an N-bit binary fraction via any known method. The binary fraction can take the form of:

$$S = 0.b_N b_{N-1} \ldots b_2 b_1,$$

where $b_x$ is a binary digit, $b_N$ is the most significant digit, and $b_1$ is the least significant digit.

One method of converting a fraction of the form $$\frac{T}{2^N}$$

to a binary fraction begins by converting the numerator, T, to binary form ($T_2$). Next, based on the number of binary digits used to express $T_2$, a number of 0's are added in front of $T_2$ so that the total number of digits in $T_2$ is equal to N. Finally, a binary point is placed in front of $T_2$ to form the binary fraction. For example, to convert the fraction 212/1024 (N=10) to a binary fraction, first the numerator, 212, is converted to binary yielding $11010100_2$. Since N=10, and the binary version of the numerator 212 only has eight digits, two 0's are prefixed to the binary version of the numerator yielding $0011010100_2$. Finally, a binary point is placed in front of the number yielding the binary fraction:

$$\frac{212}{1024} = 0.0011010100_2.$$

At step 208, any 0's to the right of the least significant 1 are discarded. In the example above, this yields S=0.00110101. The remaining bit pattern, S, will serve as instructions for the remainder of the algorithm.

Continuing at step 210, the sequence of mix/split steps begins with mixing a droplet of sample/reagent fluid (having a CF of $$\frac{2^N}{2^N}$$

or 100%) with a droplet of buffer solution (having a CF of $$\frac{0}{2^N}$$

or 0%) to produce a current resultant mixture. When two fluids are mixed at a 1:1 ratio, the CF of the resultant mixture can be calculated by taking the average of the CFs being mixed. To the extent that the CFs can be expressed with identical denominators, the resultant CF will have the same denominator as the two CFs being mixed, and a numerator taken as an average of the two numerators of the CFs being mixed. For example, when a unit-volume of buffer solution with a CF expressed as:

$$\frac{0}{1024}$$

is mixed with a unit-volume of sample/reagent fluid with a CF expressed as:

$$\frac{1024}{1024},$$

the resultant mixture would be 2 unit-volumes of fluid with a CF expressed as:

$$\frac{\frac{(0+1024)}{2}}{1024} = \frac{512}{1024}$$

It should be understood that a 1:1 ratio may be any ratio in which both reactants have about equal volumes. Thus, a 1:1 ratio encompasses a 2:2, 3:3, or k:k ratio (where k is a whole number).

After mixing in step 208, the resultant mixture may be split (step not shown in FIG. 2A). For example, when one unit-volume fluid is mixed with another unit-volume fluid, the resultant mixture will have a volume of about two unit-volumes. In some cases, only a single unit-volume of the resultant mixture is desired for a subsequent mixing step. Thus, the two unit-volume mixture may be split into two unit-volume droplets, and one droplet may be discarded, or stored for later use.

After mixing in step 210, the least significant 1 of the N-bit binary fraction is discarded and the flow continues at step 212 where the least significant bit of the remaining bit pattern is checked. In the case where the least significant bit is a 0, the flow continues at step 214 where one unit-volume droplet of the current resultant mixture is mixed with one unit-volume droplet of the buffer solution to form a new resultant mixture. In the case where the least significant bit is a 1, the flow continues at step 216 where one unit-volume droplet of the current resultant mixture is mixed with one unit-volume droplet of the sample/reagent fluid to form a new resultant mixture.

After either of the mixing steps 214 or 216, and another possible splitting step (not shown in FIG. 2A), the flow continues at step 218 where the least significant bit of the remaining bit pattern bit is discarded. At step 220 a check of the remaining bits is performed. If there are still bits to the right of the binary point after discarding the least significant bit in the bit pattern, then in step 212, the new least significant bit will be used as a basis to decide which of the sample/reagent fluid or buffer solution will be mixed in the next mix step with a one unit-volume droplet of the current resultant mixture. If however, the least significant bit discarded in step 216 was the last bit in the bit pattern, then the flow ends.

Figure 3:
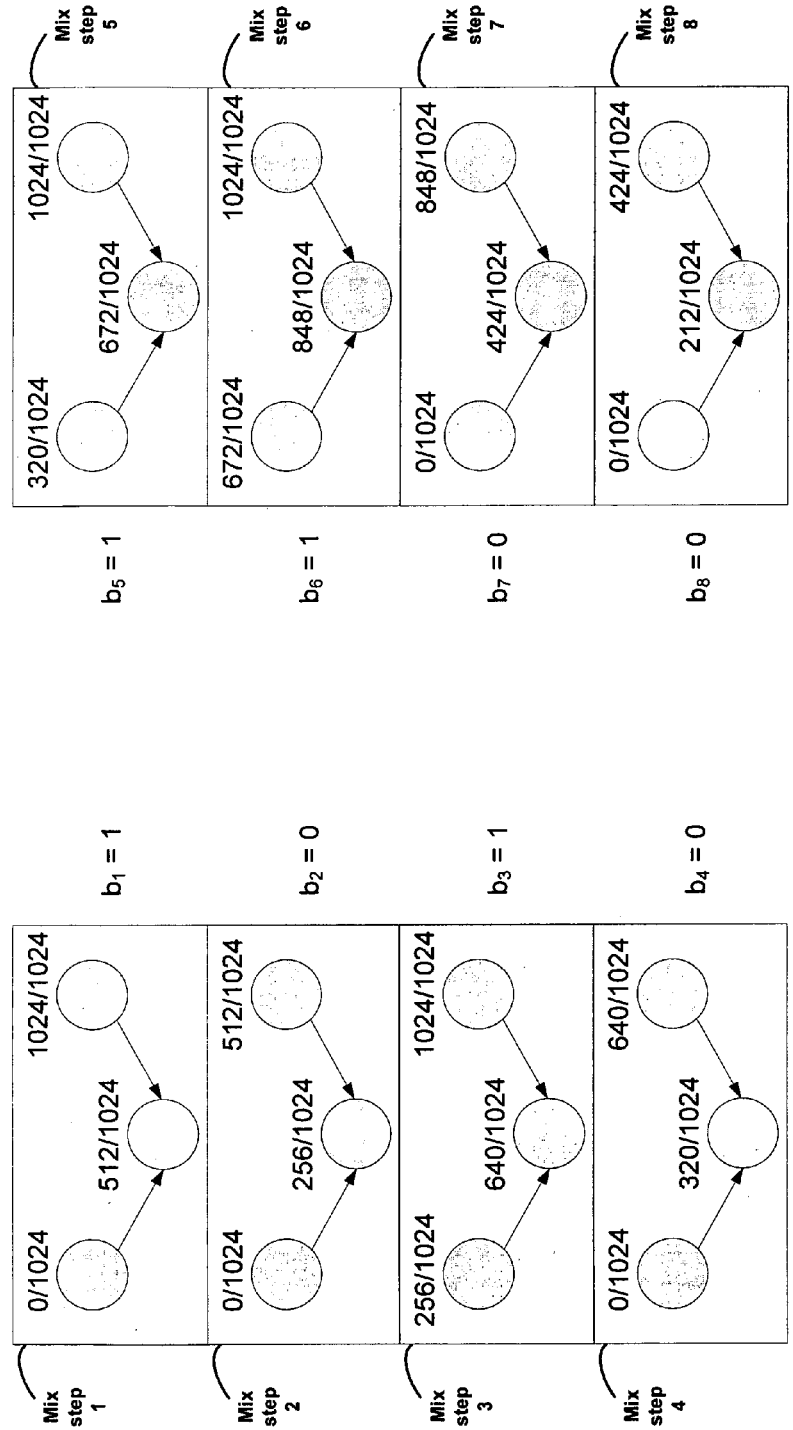
FIG. 3 is an example sequence of mix steps used to produce a fluid droplet with a specific target concentration factor.

FIG. 3 illustrates an example sequence of mix steps according to the algorithm described in flow chart 200. In this example, 10 is chosen as the precision level, and therefore all the CFs are expressed with denominators of $2^{10}=1024$. The target CF is chosen as 212/1024 and can be expressed as the binary fraction $0.0011010100_2$. After discarding any 0's to the right of the least significant 1, the remaining bits of the binary fraction result in $S=0.00110101_2$.

The example sequence of mix steps begins with mix step 1, where the buffer solution (CF of 0/1024) and sample/reagent fluid (CF of 1024/1024) are mixed at a 1:1 ratio. Since the two input fluids for this mix step, and in each mix step, are mixed at a 1:1 ratio, the CF of the current resultant mixture can be calculated by taking the average of the CF numerators of the input fluids. In mix step 1, for example, the resultant mixture CF numerator, 512, is the average of the buffer solution CF numerator, 0, and the sample/reagent fluid CF numerator, 1024.

After mix step 1, the least significant 1 is discarded and the next least significant bit of the remaining bits of the binary fraction, S, is checked. In the example, the next least significant bit of S (denoted as $b_2$) is a 0. Therefore, in mix step 2, the resultant mixture from the previous mix step (mix step 1) is mixed with the 0/1024 buffer solution to produce a new current resultant mixture with a CF of 256/1024. The next least significant bit of S (denoted as $b_3$) is checked and determined to be a 1. Consequently, in the next mix step, mix step 3, the resultant mixture from the previous mix step (mix step 2) is mixed with the 1024/1024 sample/reagent fluid to produce a new current resultant mixture with a CF of 640/1024.

The mix steps in FIG. 3 proceed in this manner, producing resultants having CFs of 320/1024 in mix step 4, 672/1024 in mix step 5, 848/1024 in mix step 6, 424/1024 in mix step 7, and finally the target CF, 212/1024 in mix step 8.

The preceding bit scanning algorithm applies to cases where the initial two fluid samples have CFs of $0/2^N$ and $2^N/2^N$ (e.g., a buffer solution and a sample/reagent fluid). In some situations, however, it may not be desirable, or even possible to obtain and use initial fluid samples with CFs of $0/2^N$ and $2^N/2^N$. Instead, what may be available for use are initial fluid samples that have CFs other than $0/2^N$ and $2^N/2^N$, such as CFs>$0/2^N$, and CFs<$2^N/2^N$. Therefore, an algorithm that produces a target CF ($C_T$) from two initial CFs (a $C_H$ and a $C_L$), where $0\%<C_L<C_T<C_H<100\%$, may also be desired.

One such algorithm for producing a target CF ($C_T$) from two initial CFs (a $C_H$ and a $C_L$), where $0\%\leq C_L \leq C_T \leq C_H \leq 100\%$, includes first mapping, or transforming, the target CF from a scale in which the boundary CFs are $C_L$ and $C_H$, to a scale in which the boundary CFs are $0/2^N$ and $2^N/2^N$. Second, the algorithm includes executing the bit scanning algorithm with respect to the transformed target CF and the boundary CFs, $C_L$ and $C_H$. This modified bit scanning algorithm is illustrated by the flow chart 250 in FIG. 2B, and is applicable to instances both where a supplied reagent fluid (or, raw sample) has a CF of 100% and a buffer solution has a CF of 0%, and where the two supplied fluids have CFs expressed as $C_L$ an $C_H$, where $0\%\leq C_L \leq C_T \leq C_H \leq 100\%$.

Figure 4:
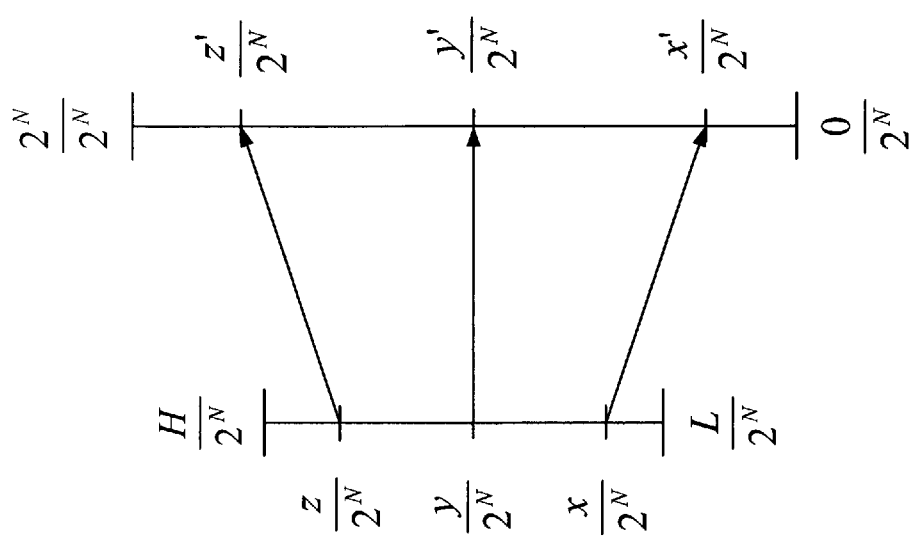
FIG. 4 is an example mapping of concentration factors in one scale to concentration factors in another scale.

The effect of transforming a target CF is illustrated in FIG. 4, where target CFs $$\frac{z}{2^N}, \frac{y}{2^N}, \text{ and } \frac{x}{2^N}$$

in the scale from $$\frac{L}{2^N} \text{ to } \frac{H}{2^N},$$

are shown mapped to $$\frac{z'}{2^N}, \frac{y'}{2^N}, \text{ and } \frac{x'}{2^N}$$

on the scale from $$\frac{0}{2^N} \text{ to } \frac{2^N}{2^N}.$$

A transformed target CF numerator, z', for example is given by the formula:

$$z' = 2^N \cdot \frac{z - L}{H - L},$$

where z is the numerator of the target CF in the original scale.

Figure 2B:
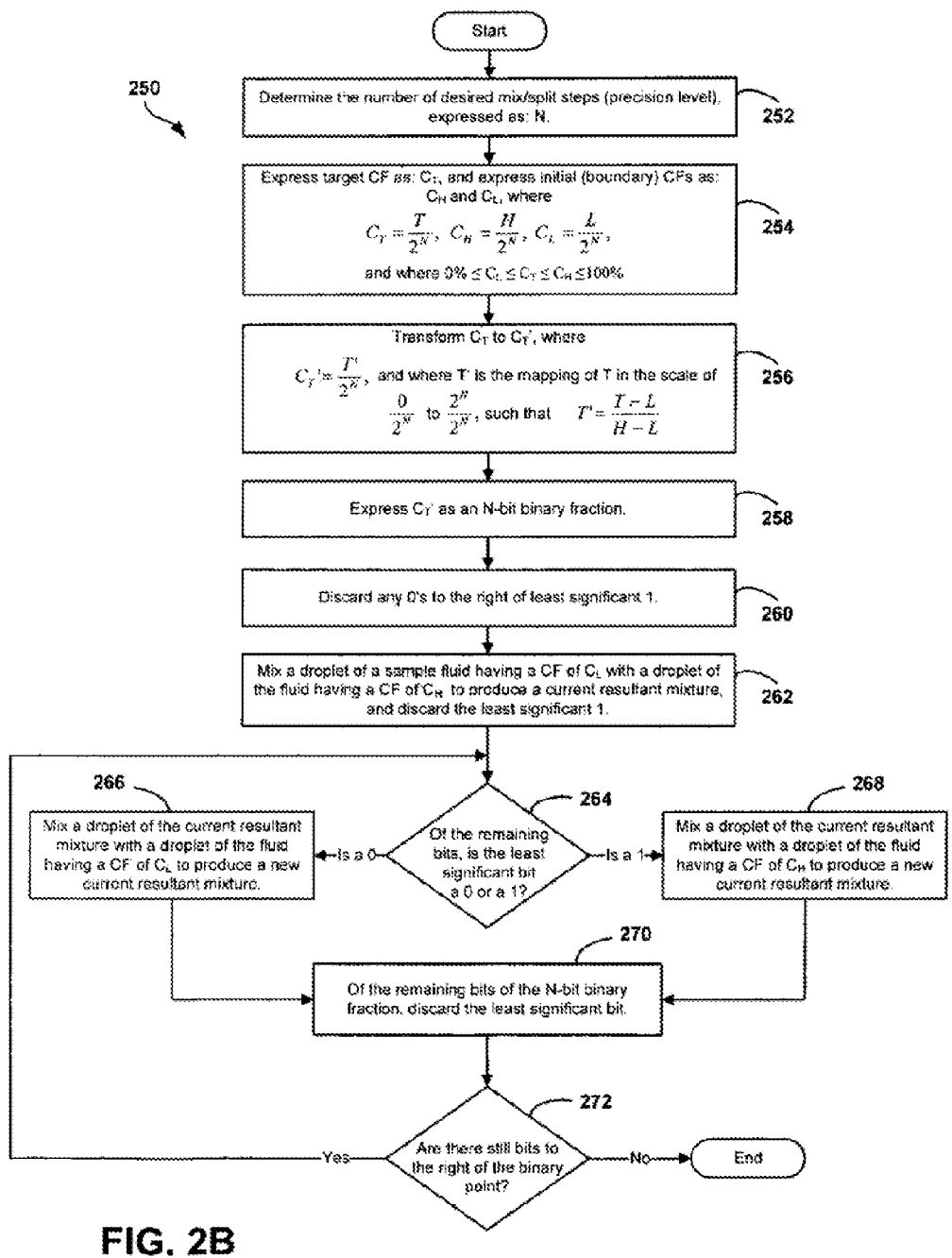
FIG. 2B is a flow chart illustrating another example algorithm for determining a sequence of mix steps used to produce a fluid droplet having a target concentration factor from the supply of a fluid having two arbitrary concentration factors (one less than 100% concentration and other greater than 0% concentration.).

The full bit scanning algorithm is illustrated by the flow chart 250 in FIG. 2B. The flow 250 begins at step 252 where the desired number of mix/split steps, N, is determined. After N (or less) mix/split steps, the algorithm produces a resultant solution having a CF equal to the target CF within an error in concentration factor of about $\pm\frac{1}{2}^N$. Therefore, N can be thought of as a precision level, since the larger N is (the more mix/split steps allowed), the more precise the target concentration can be.

In the next step 254, the target CF and initial (boundary) CFs are each expressed as rational numbers with denominators of $2^N$, such as:

$$C_T = \frac{T}{2^N},$$

$$C_H = \frac{H}{2^N},$$

$$C_L = \frac{L}{2^N}$$

where N is a whole number. The numerator of the target CF can be expressed as T, where T is a whole number, and where $0\% \leq C_L \leq C_T \leq C_H \leq 100\%$.

Continuing at step 256, the target CF, $C_T$, is transformed to $C_T'$, via the formula:

$$C_T' = \frac{T'}{2^N} = \frac{T - L/H - L}{2^N}.$$

This transforms the target CF from a scale of $$\frac{L}{2^N} \text{ to } \frac{H}{2^N},$$

to a scale of $$\frac{0}{2^N} \text{ to } \frac{2^N}{2^N}.$$

The transformed target CF, $C_T'$, can then be used in the remainder of the bit scanning algorithm to produce target droplets having the original target CF, $C_T$.

In step 258, the transformed target CF is expressed as an N-bit binary fraction via any known method. The binary fraction may take the form of:

$$S = 0 \cdot b_N b_{N-1} \ldots b_2 b_1,$$

where $b_x$ is a binary digit, $b_N$ is the most significant digit, and $b_1$ is the least significant digit.

At step 260, any 0's to the right of the least significant 1 are discarded. The remaining bit pattern, S, will serve as instructions for the remainder of the algorithm.

Continuing at step 262, the sequence of mix/split steps begins with mixing one unit-volume droplet of $C_L$ with one unit-volume droplet of $C_H$ to produce a current resultant mixture. When two fluids are mixed at a 1:1 ratio, the CF of the resultant mixture can be calculated by taking the average of the CFs being mixed.

After mixing in step 262, the resultant mixture may be split (step not shown in FIG. 2B). For example, when one unit-volume fluid is mixed with another unit-volume fluid, the resultant mixture will have a volume of about two unit-volumes. In some cases, only a single unit-volume of the resultant mixture is desired for a subsequent mixing step. Thus, the two unit-volume mixture may be split into two unit-volume droplets, and one droplet may be discarded, or stored for later use.

After mixing in step 262, the least significant 1 of the N-bit binary fraction is discarded and the flow continues at step 264 where the least significant bit of the remaining bit pattern is checked. In the case where the least significant bit is a 0, the flow continues at step 266 where one unit-volume droplet of the current resultant mixture is mixed with one unit-volume droplet of the fluid having a CF of $C_L$ to form a new resultant mixture. In the case where the least significant bit is a 1, the flow continues at step 268 where one unit-volume droplet of the current resultant mixture is mixed with one unit-volume droplet of the fluid having a CF of $C_H$ to form a new resultant mixture.

After either of the mixing steps 266 or 268, and another possible splitting step (not shown in FIG. 2B), the flow continues at step 270 where the least significant bit of the remaining bit pattern bit is discarded. At step 272 a check of the remaining bits is performed. If there are still bits to the right of the binary point after discarding the least significant bit in the bit pattern, then in step 264, the new least significant bit will be used as a basis to decide which of the sample/reagent fluid or buffer solution (or the fluid with CFs of $C_H$ or $C_L$) will be mixed in the next mix step with a one unit-volume droplet of the current resultant mixture. If however, the least significant bit discarded in step 270 was the last bit in the bit pattern, then the flow ends.

Figure 5:
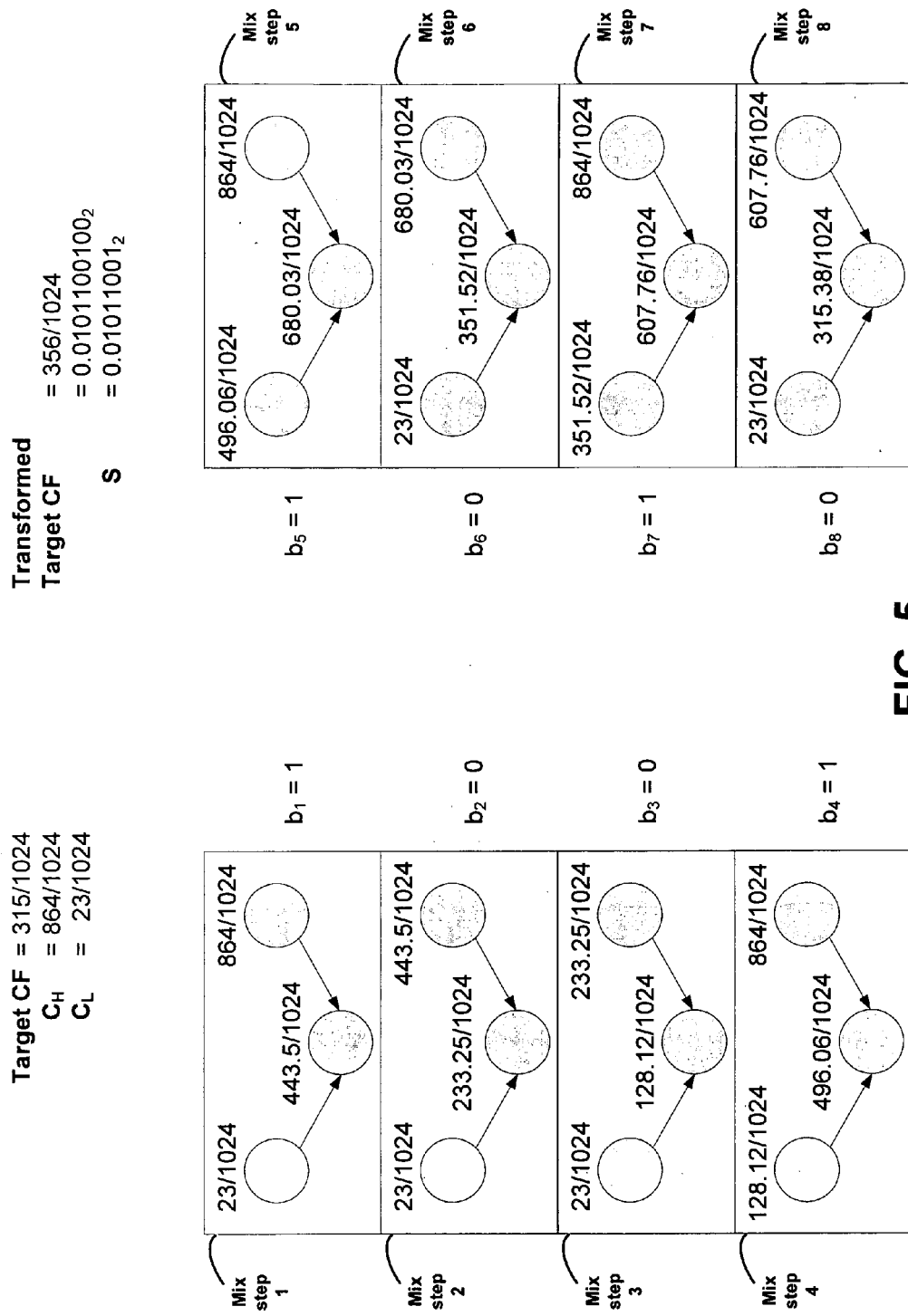
FIG. 5 is another example sequence of mix steps used to produce a fluid droplet with a specific target concentration factor.

FIG. 5 illustrates an example sequence of mix steps according to the algorithm described in flow chart 250. In this example, a target CF of $$\frac{315}{1024}$$

is desired to be produced from boundary CFs $$\frac{864}{1024} \text{ and } \frac{23}{1024}.$$

First, the target CF is transformed to $$\frac{C'_T}{1024},$$

where $C'_T$ is determined via the formula described above, yielding:

$$C'_T = 1024 \cdot \frac{315 - 23}{864 - 23} \approx 356,$$

and thus yielding a transformed target CF of $$\frac{356}{1024}.$$

Next, the transformed target CF is converted to a binary fraction and the least significant 1 and any 0's to the right of the least significant 1 are discarded, thus yielding:

$$S = 0.0101100_2.$$

Finally, a sequence of mix steps is carried out with respect to the binary fraction, S, and the initial boundary CFs $$\frac{864}{1024} \text{ and } \frac{23}{1024}.$$

The sequence begins at mix step 1 where the two boundary CFs are mixed together producing a resultant CF of 443.5/1024. Since the least significant bit of the binary fraction, S, is a 0, in the next mix step (mix step 2) the lower boundary CF (23/1024) is mixed with the resultant of the previous mix step (mix step 1) producing a new resultant CF of 223.25/1024. The sequence continues at mix step 3 where the 223.25/1024 CF is mixed with the lower boundary CF 23/1024 as a result of the next least significant bit of S being a 0.

The mix steps in the example of FIG. 5 proceed in this manner, producing resultants having CFs of 496.06/1024 in mix step 4, 680.03/1024 in mix step 5, 351.52/1024 in mix step 6, 607.76/1024 in mix step 7, and finally, in mix step 8, the final target CF of 315.38/1024 (which is within an acceptable error of ±1/1024 from the original target CF of 315/1024).

When implemented in a DMF biochip, the bit scanning algorithm can produce two unit-volume droplets of the target CF without requiring any storage of any intermediate CFs (or in other examples with minimal or no storage of intermediate CFs). This is because at each given mix step in the algorithm, only one of the two droplets produced in the previous mix step is required for the given mix step. That required droplet can remain in a mixing module to be mixed with one of the supplied inputs of two boundary CFs, for example, and the other droplet can be discarded.

Figure 6:
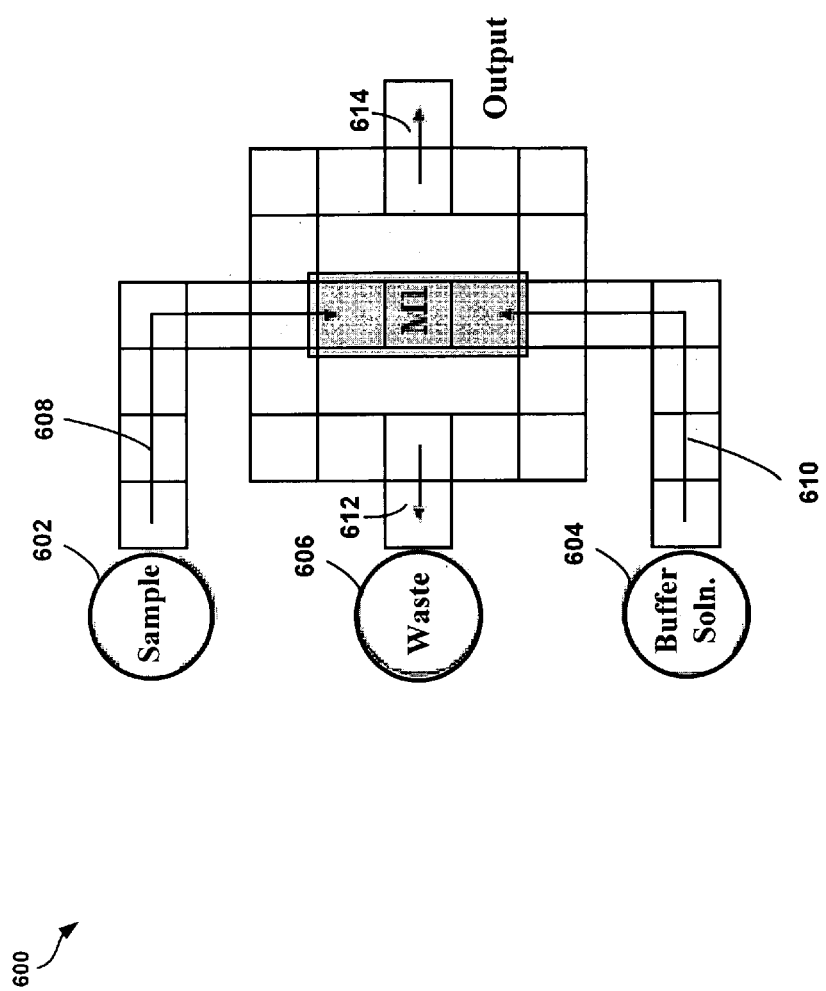
FIG. 6 is an example arrangement of DMF-based electrode platforms for carrying out a sequence of mix steps for dilution of a fluid.

FIG. 6 illustrates an example arrangement 600 of EWOD platforms that may comprise a digital microfluidic biochip able to carry out a sequence of mix/split steps according to the bit scanning algorithm. The arrangement includes a sample reservoir 602, a buffer reservoir 604 (or second sample reservoir), and a waste reservoir 606. The arrangement includes only one mixing module M1 to carry out mixing and splitting steps. The mixing module M1 is configured as a 1×3 array of platforms, but other platform configurations could be used as well. This type of mixing module performs mixing steps relatively quickly by using a number of merge and split operations. Mixing module M1 can split a droplet volume of twice the unit-volume into two droplets of one unit-volume each.

The arrangement 600 also includes a plurality of platforms that surround the rotary mixer 616 and form pathways for droplets to travel to and from the reservoirs. For example, a plurality of platforms form sample pathway 608 and are able to transport droplets between the sample reservoir 602 and the mixing module M1. A plurality of platforms forming sample pathway 610 is able to transport droplets between sample reservoir 604 and mixing module M1. A plurality of platforms forming waste pathway 612 is able to transport droplets to the waste reservoir 606, and a plurality of platforms forming output pathway 614 is able to transport droplets to an output, such as outside the biochip.

To carry out a sequence a mix steps, for example the mix steps of FIG. 3, sample reservoir 602 may be supplied with an adequate amount of one boundary CF (e.g., 1024/1024), and sample reservoir 604 may be supplied with an adequate amount of the other boundary CF (e.g., 0/1024). The first mix step in the sequence of mix steps of FIG. 3 may be carried out by actuating the platforms of sample pathway 608 and sample pathway 610 so as to transport a droplet from each of sample reservoirs 602 and 604 to the mixing module M1. When both initial droplets arrive at mixing module M1, an appropriate actuation sequence may cause the platforms of mixing module M1 to mix the droplets together, thus forming the resultant mixture droplet of 2 unit volumes, having a CF of 512/1024.

An appropriate actuation sequence may then cause the mixing module M1 to split the resultant mixture into two unit-volume droplets and transport one of the two droplets to waste reservoir 606 via waste pathway 612 (and other intermediate platforms). The other of the two unit-volume droplets may remain at mixing module M1 to be mixed in the next mixing step (mix step 2) after a further actuation sequence causes a 0/1024 CF droplet to be transported from sample reservoir 604 to mixing module M1 via sample pathway 610. An appropriate actuation sequence at mixing module M1 may then cause the 512/1024 CF droplet and the 0/1024 CF droplet to mix in mix step 2, thus producing a 256/1024 CF resultant mixture. This resultant mixture may then be split into two unit-volume droplets at the module M1, and one 256/1024 droplet may be transported to waste reservoir 606 while the other 256/1024 droplets remains at the mixing module M1 for the mix step 3.

The mix steps of FIG. 3 continue in this manner by actuating the platforms of arrangement 600 in appropriate sequences. When the final mix step takes place, producing two unit-volume droplets of the target CF (212/1024 in the example sequence of mix steps of FIG. 3), the mixing module M1 may split the droplets and transport them via output path 614.

The bit scanning algorithm yields two unit-volume droplets after n mix steps. The lowercase notation, 'n', may represent the actual number of mix steps used to produce a target CF from two boundary CFs, while the uppercase notation, 'N', may represent the precision value of the target CF. In the example sequence of mix steps of FIG. 3 and FIG. 5, 'N' is chosen as 10, while the number of mix steps used to reach the target CF, 'n', is 8. The time it takes to complete a mix step is considerably longer than the time it takes to transport droplets to/from the reservoirs and mix modules. Therefore, this transport time may be regarded as negligible when considering the total time used to carry out a sequence of mix steps. The total time used to carry out a sequence of mix steps may then be thought of in terms of a number of "time steps," where one time step is the time used to complete a mixing step. Thus, the example sequence of mix steps of FIG. 3 or FIG. 5, when carried out on a DMF biochip or other arrangement of DMF-based electrode platforms such as the arrangement 600, may produce two unit-volume droplets of the target CF after eight time steps.

Figure 7:
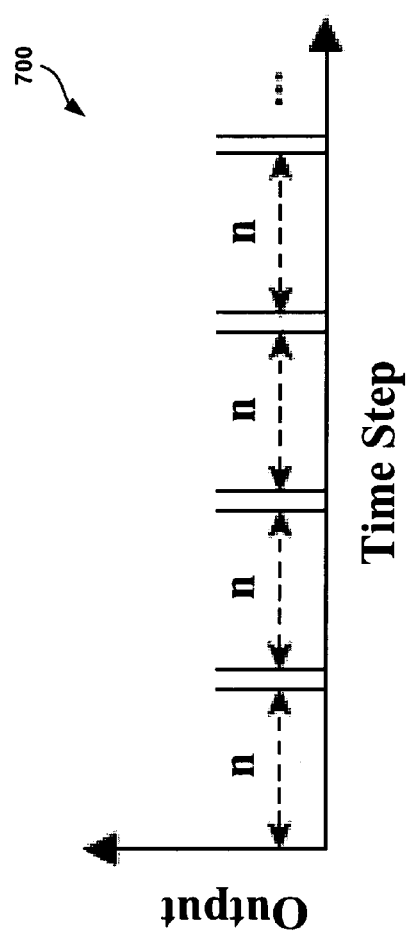
FIG. 7 is an example timing diagram illustrating the time steps used to produce target CF droplets according to the proposed algorithm executed on the layout of FIG. 6.

In practice, it may be desired that more than two unit-volume droplets of the target CF be produced from the two boundary CFs. One simple way to produce an additional two target droplets is to repeat the sequence of mix steps from the beginning. This is illustrated in FIG. 7 by the timing diagram 700. For every two target CF droplets desired, n time steps may be used. Each output droplet is illustrated on the timing diagram 700 as a vertical spike, and thus a total of two output droplets are produced after n time steps, a total of four output droplets are produced after 2n time steps, a total of six after 3n time steps, etc.

An alternative way to produce additional target CF droplets from a sequence of mix steps determined by a bit scanning algorithm includes storing one or more of the resultant droplets produced in the intermediate mix steps instead of discarding them. After two target CF droplets are produced from the original sequence of mix steps, a portion of the original sequence may be repeated starting with the stored intermediate droplet. In this manner, two additional target CF droplets can be produced in fewer number of total mix steps than if the entire sequence was repeated.

Figure 8:
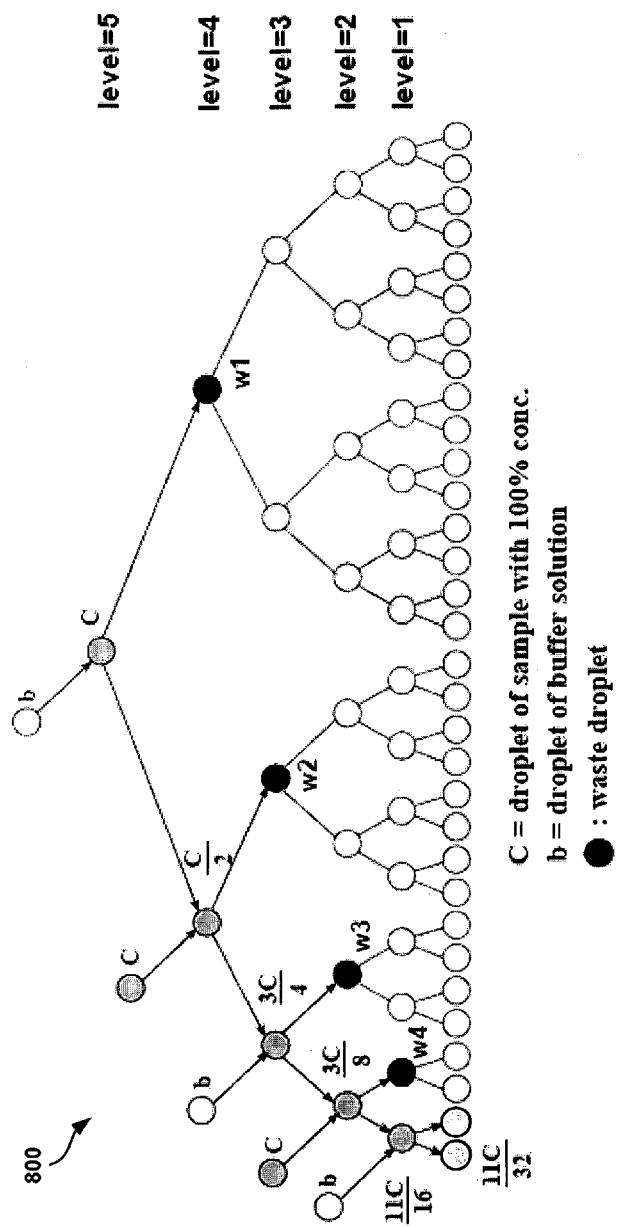
FIG. 8 is an example mix/split tree illustrating a sequence of mix and split steps used to produce a desired target CF.

FIG. 8 illustrates a mix/split tree 800 for a sequence of mix steps that produce target droplets of 11/32 CF from boundary CFs of 0/32 (referred to as in FIG. 8) and 32/32 (referred to as 'C' in FIG. 8). The sequence commences in mix step 1 by mixing a droplet of 0/32 with a droplet of 32/32 forming a C/2, or 16/32, CF mixture. The node corresponding to the mix step 1 is at level 5 of the mix/split tree 800 of height 5, since it is the first of a 5 mix step sequence. Next at level 4, a droplet of the 16/32 mixture is mixed with the 32/32 boundary CF, forming a 3C/4, or 24/32, CF mixture. At level 3, a droplet of the 24/32 is mixed with a droplet of 0/32 to form a 3C/8, or 12/32, CF mixture, and at level 2, a droplet of the 12/32 mixture is mixed with a droplet of the 32/32 mixture to form a 11C/16, or 22/32, CF mixture. Finally, at level 1 (or mix step 5) a droplet of the 22/32 mixture is mixed with a droplet of the 0/32 mixture to form two droplets of the target CF 11/32.

Depending on the desired number of target droplets, one or more of the waste droplets produced at levels 1-5 (i.e., w1, w2, w3, and w4) can be stored and used in repeat mix steps. For example, if 3 or 4 target droplets are desired, then the level 1 mix step may be repeated using the waste droplet produced at level 2 (i.e., the waste droplet produced in the $2^{nd}$ to the last mix step), w4, thus forming an additional two target CF droplets.

Similarly, if 5, 6, 7, or 8 target CF droplets are desired, then w3 is stored after level 3 and w4 is stored after level 2. Following the level 1 mix step producing the first two target CF droplets, the level 1 mix step may be repeated using w4, thus forming an additional two target CF droplets. Then, the level 2 mix step may be repeated using w3, thus forming two 11/16 CF droplets. Depending on whether 5, 6, 7, or 8 target CF droplets are desired, the subsequent level 1 mix step may be carried out once or twice. For example, if 5 or 6 droplets are desired, then the level 1 mix step may be carried out only once, and so one of the 11/16 CF droplets may be discarded. However, if 7 or 8 target CF droplets are desired, then the subsequent level 1 mix step may need to be repeated twice for both the 11/16 CF droplets, and so one 11/16 CF droplet needs to be stored rather than discarded.

It can be seen from the mix/split tree 800 that the sequence of mix split steps starting at each level can be repeated with the waste droplets from the preceding mix steps to generate multiple (i.e., more than 2) target CF droplets. Since, in this example, there are 5 levels (or 5 original mix steps used to produce the first two target CF droplets), storing each of the four waste droplets produced in the original sequence of mix steps, and subsequently repeating the mix steps using the waste droplets (and using the additional waste droplets produced thereafter), up to $2^5$, or 32, total target CF droplets may be produced. This can be generalized and extended to sequences with any number of mix steps. For example, in a sequence of n mix steps, a maximum of $2^n$ target droplets can be produced using the described roll-back method. In order to produce M target droplets, where M≤$2^n$, waste droplets produced at the $j^{th}$ level mix step (i.e, the $j^{th}$-to-last mixing step), and waste droplets produced at each step thereafter should be stored, where j is expressed as:

$$j = \lceil \log_2 M \rceil.$$

Figure 9:
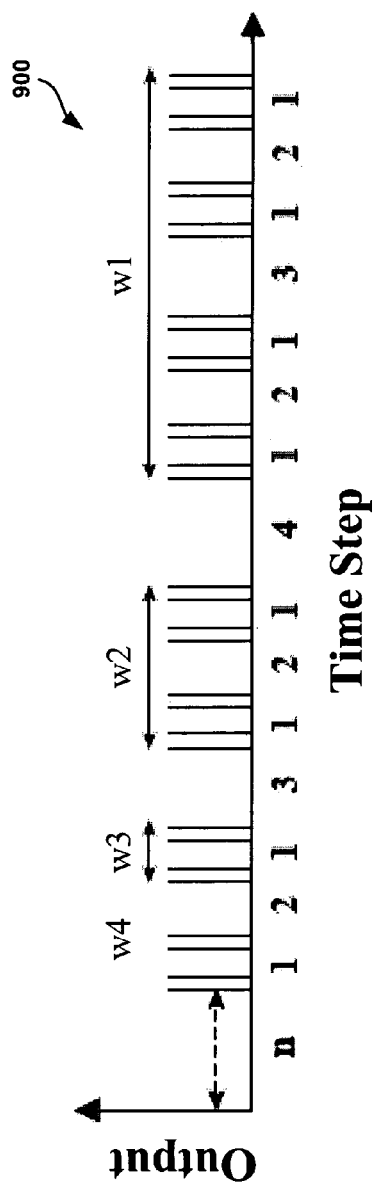
FIG. 9 is another example timing diagram illustrating the time steps used to produce target CF droplets according to the proposed algorithm executed on the layout of FIG. 11.

FIG. 9 is a timing diagram 900 that illustrates the time steps used to produce each of the $2^5$ target CF droplets according to the roll-back method i.e., the method of reusing the stored waste droplets described above. To produce the first two target CF droplets, n, or 5 in the case of the example of FIG. 8, time steps may be used. Using the most recently stored waste droplet, w4, one additional time step is used to produce an additional two target CF droplets. Using the next most recently stored waste droplet, w3, two more time steps are used to produce a further additional two target CF droplets and one more time step is used to produce a still further additional two target CF droplets. Repeating the sequence of mix steps further with the next most recently stored waste droplet, w2, seven more time steps are used to produce an additional eight target CF droplets. Re-executing the sequence of mix steps still further with the last stored waste droplet, w1, an additional 15 time steps are required to produce all of the 16 remaining target CF droplets. It should be understood that the timing diagram 900 illustrates the time steps used to produce the first 32 target droplets according to the method of reusing stored waste droplets and may be extended to produce additional droplets depending on the number of original mix steps, n, and the number of stored waste droplets.

Figure 10:
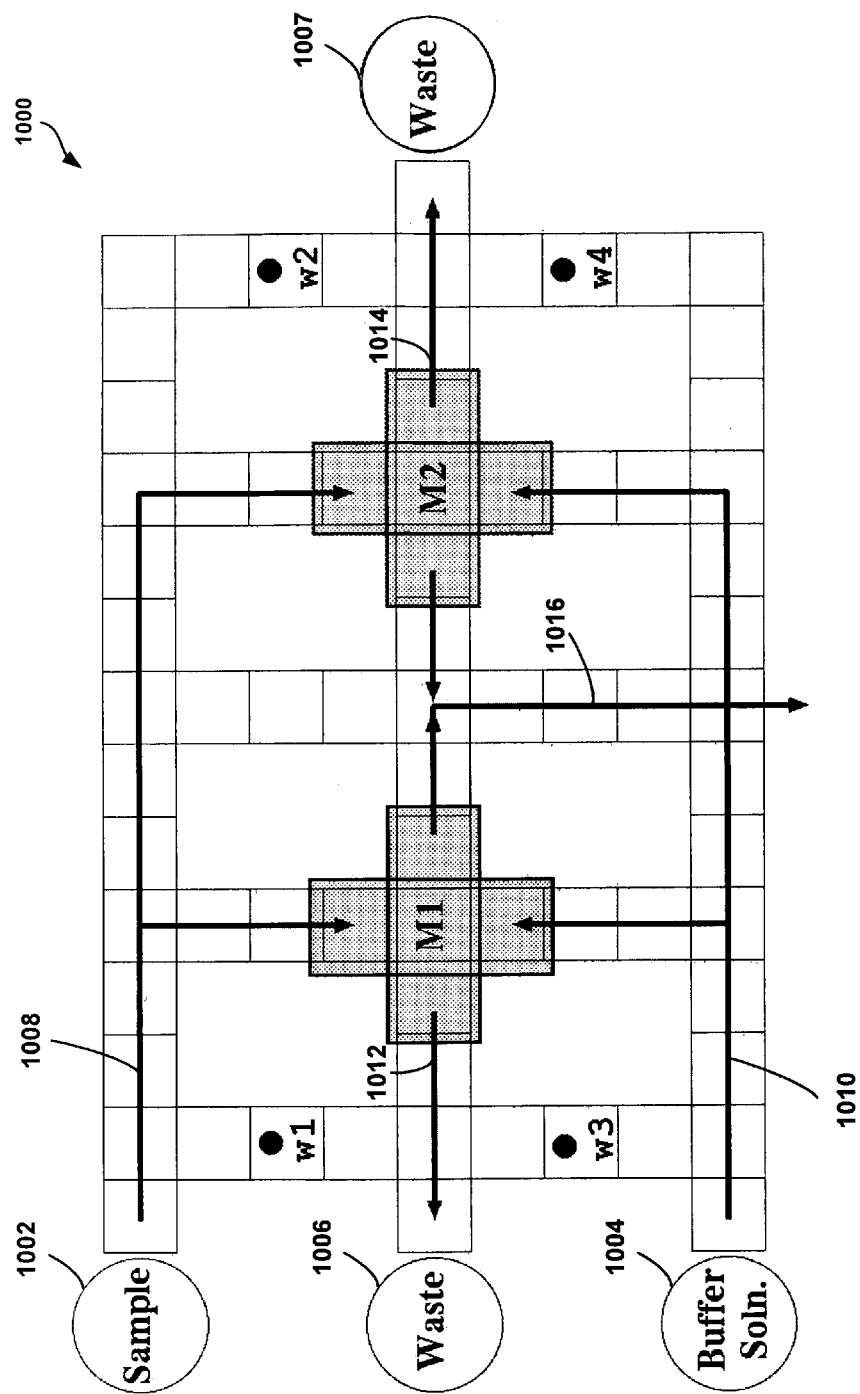
FIG. 10 is another example arrangement of DMF-based electrode platforms for carrying out a sequence of mix steps for dilution with a lower precision level allowing maximum of 4 mix/split steps with storages.

FIG. 10 illustrates an example arrangement 1000 of DMF-based electrode platforms that may comprise a digital microfluidic biochip able to carry out a sequence of mix steps according to both the original and modified bit scanning algorithms for 1 or 2 target CF droplets or for continuous emission of target CF droplets by reusing the stored waste droplets. The arrangement 1000 includes a sample reservoir 1002, a buffer reservoir 1004 (or second sample reservoir), and waste reservoirs 1006 and 1007. The arrangement 1000 also includes two split-and-merge type mixing modules M1 and M2 to carry out the mixing and splitting steps.

The arrangement 1000 also includes a plurality of platforms that surround the mixing modules M1 and M2 and form pathways for droplets to travel to and from the reservoirs. For example, a plurality of platforms form sample pathway 1008 and are able to transport droplets between the sample reservoir 602 and the mixing modules M1 and M2. A plurality of platforms forming sample pathway 1010 are able to transport droplets between sample reservoir 1004 and mixing modules M1 and M2. A plurality of platforms forming waste pathways 1012 and 1014 are able to transport droplets to respective waste reservoirs 1006 and 1007, and a plurality of platforms forming output pathway 1016 are able to transport droplets to an output, such as outside the biochip.

Certain platforms in the arrangement 1000 may be used as storage platforms. The storage platforms can hold droplets that are produced in intermediate mixing steps and are needed again in repeat mixing steps by reusing the stored waste droplets. Possible storage platforms in arrangement 1000 are identified with black dots. Since the arrangement 1000 includes four storage platforms, it can be used with mixing sequences of 5 or less steps, such as the sequence of FIG. 8. In addition to being identified with a black dot, the storage platforms indicate which waste droplet (such as the waste droplets w1, w2, w3, and w4 of the example sequence of mix steps of FIG. 8) can be optionally stored there (though this is an example and should not be seen as limiting).

Figure 11:
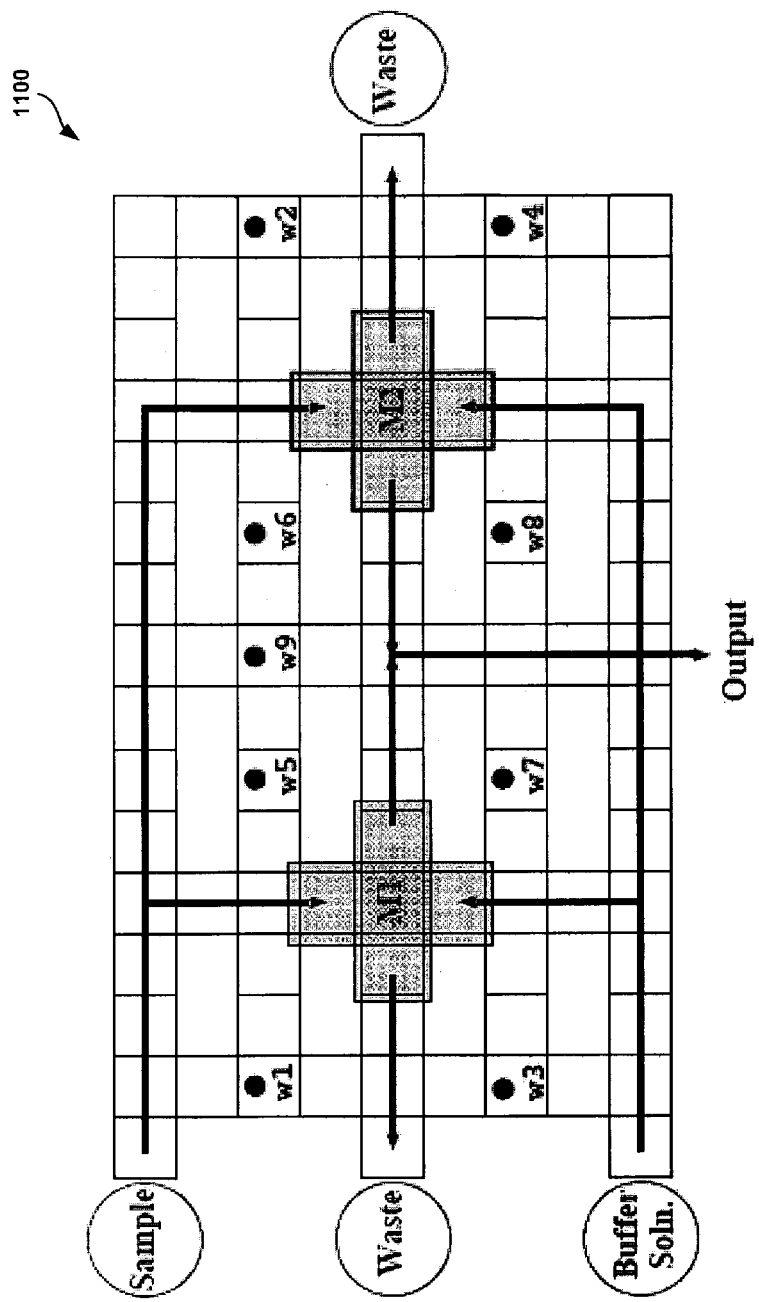
FIG. 11 is another example arrangement of DMF-based electrode platforms for carrying out a sequence of mix steps for dilution with a higher precision level allowing maximum of 10 mix/split steps with storages.

The number of storage platforms in an arrangement of DMF-based electrode platforms designed to carry out both the original and modified bit scanning algorithm and the roll-back method may be one less than the number of determined steps for a given application. For example, the arrangement 1000 includes one less than 5 storage locations and can be used with the example sequence of mix steps of FIG. 8. Arrangement 1100 in FIG. 11 includes one less than 10 storage locations and can be used in applications requiring up to 9 storage locations (such as applications with 10 or less mix steps).

The arrangements 1000 and 1100 are shown having a mixing module M1 and an optional additional mixing module M2. The second mixing module M2 may be included to take advantage of parallel processing and reduce the inter-step droplet transportation time. For example, the arrangement 1100 may carry out the example sequence of mix steps illustrated in FIG. 3. One mixing module, say M1, may be designated to carry out the first mix step where a droplet of 0/1024 is mixed with a droplet of 1024/1024. Simultaneous to mix step 1 occurring at mixing module M1, the boundary CF used in mix step 2 (0/1024) may be transported to mixing module M2 so that upon completion of mix step 1 at mixing module M1, a resultant droplet can be immediately transported to mixing module M2 where mix step 2 can take place. This alternating of mix steps at each mixing module may increase the speed at which the resultant droplets are produced.

Similarly, the arrangement 1100 may carry out the example sequence of mix steps illustrated in FIG. 5. One mixing module, say M1, may be designated to carry out the first mix step where a droplet of 23/1024 is mixed with a droplet of 864/1024. Simultaneous to mix step 1 occurring at mixing module M1, the boundary CF used in mix step 2 (23/1024) may be transported to mixing module M2 so that upon completion of mix step 1 at mixing module M1, a resultant droplet can be immediately transported to mixing module M2 where mix step 2 can take place. This alternating of mix steps at each mixing module may increase the speed at which the resultant droplets are produced.

Additionally, when executing a roll back sequence, each mixing module can be used to carry out steps of the roll-back sequence at the same time. For example, after producing two target CF droplets, an additional six target CF droplets may be desired. Mixing module M1 may recall the most recently stored waste droplet and repeat the last mixing step of a determined sequence of mix steps, thus producing two additional target droplets. Simultaneously, mixing module M2 may recall the next most recently stored waste droplet and repeat the second-to-last mixing step of the determined sequence of mix steps, thus producing two resultant droplets. One resultant droplet may remain at mixing module M2 while the other resultant droplet may be transferred to mixing module M1. Then, each mixing module may repeat the last mixing step of the determined sequence of mixing steps, thus producing an additional four target CF droplets.

On DMF biochips, variations in droplet volume may arise after dispensing droplets from a reservoir or after splitting resultant mixtures. When droplets of unequal volumes are mixed, the actual CF of the resultant mixture may be different than an expected CF, especially after a volume variation is compounded over several mixing and splitting steps. In order to help solve this problem, capacitive sensing circuits may be included in some of the arrangement of electrodes nearby to the dispensing ports and the mix/split modules.

A capacitance formed at the DMF-based electrode platform 1202 illustrated in FIG. 12A, may be used to help determine the relative volume of a droplet that is held on that electrode. For example, the volumetric error detection electrode 1202 shown in FIG. 12A may be integrated with circuitry 1204 illustrated in FIG. 12B. The circuitry 1204 may measure the capacitance between the two electrodes of platform 1202 and produce an output voltage waveform, such as waveform 1206 of FIG. 12C corresponding to the normal volume of a droplet. Voltage waveforms of similar magnitude may indicate similar droplet volumes, while voltage waveforms of differing magnitudes may indicate different droplet volumes. For example, waveform 1208 of FIG. 12D may indicate a droplet volume greater than that indicated by waveform 1206. Likewise, waveform 1210 of FIG. 12E may indicate a droplet volume less than that indicated by waveform 1206.

The capacitance (C) that results from a particular droplet being held on a DMF-based electrode platform may be expressed by the following equation:

$$C = \frac{\varepsilon \cdot A}{d},$$

where '$\varepsilon$' is the permittivity of the droplet confined between top and bottom electrodes, 'A' is the area overlap by the droplet between the top and bottom electrodes, and is the distance between the top and bottom electrodes (gap-height of the DMF chip).

Figure 13:
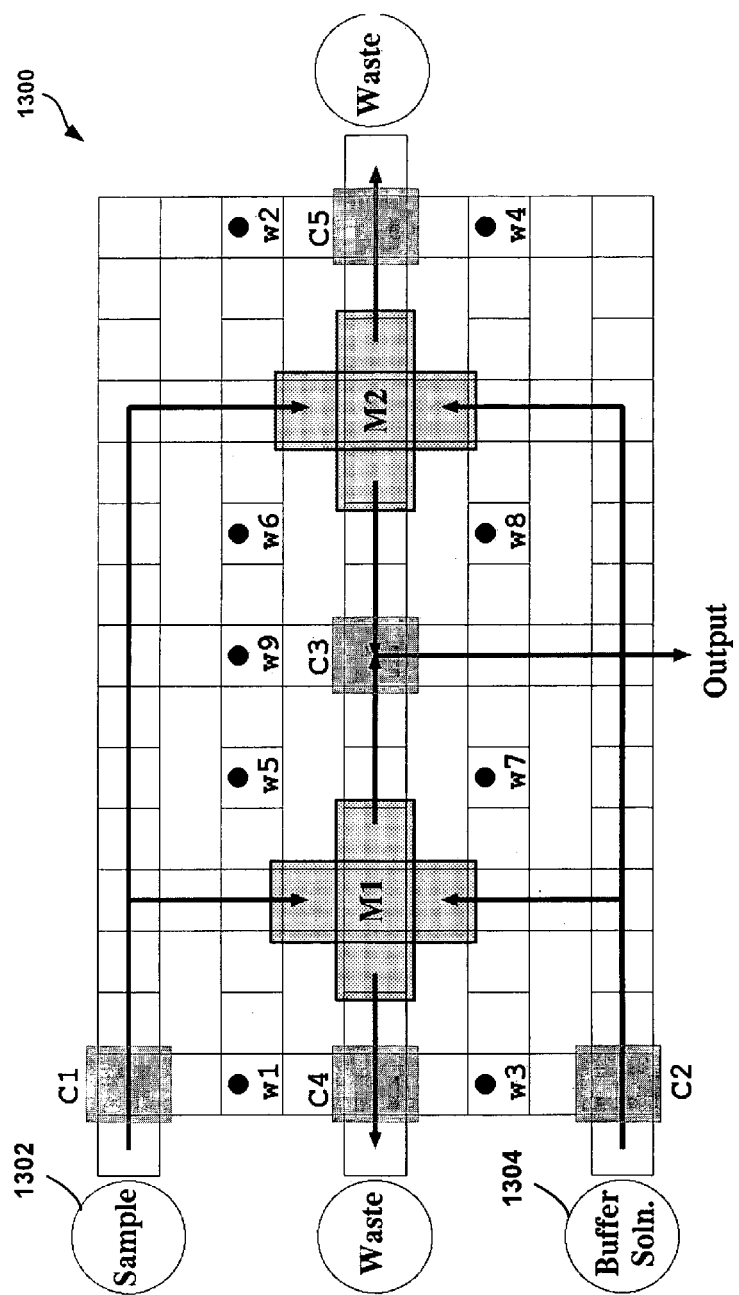
FIG. 13 is an example arrangement of DMF-based electrode platforms for carrying out a sequence of mix steps for volumetric error resilient dilution of fluid that includes five capacitive sensing circuit associated electrodes.

FIG. 13 illustrates an arrangement 1300 of DMF-based electrode platforms similar to the arrangement 1100. The arrangement 1300 includes capacitive sensing circuits C1, C2, C3, C4, and C5 associated with the five indicated electrodes. It should be understood that the illustrated position of the electrodes associated with the capacitive sensing circuits in FIG. 13 should not be limiting, and any platform on an arrangement of platforms may be attached to a capacitive sensing circuit.

The capacitive sensing circuit C1, for example, may be used to test the volume of droplets dispensed from sample reservoir 1302. The capacitive sensing circuit C1 may be first calibrated by dispensing two or more test droplets of normal volume to C1 and taking an average of two or more readings (e.g., magnitudes of voltage waveforms) resulting from each of the dispensed droplets. Then, readings from droplets dispensed by sample reservoir 1302 during a sequence of mix steps may be compared to the calibrated value of normal volume of a sample droplet. If the difference in voltages (measured by a differential amplifier) between the reading of a droplet dispensed during a sequence of mix steps and the reading of a normal volume droplet does not fall within an allowable error threshold (e.g., 7%, depending on the application requirement) of a previously calibrated value, then that droplet may be discarded and a new droplet dispensed. If the volumetric error in the reading of a particular dispensed droplet falls within the allowable error threshold of the calibrated value, then that dispensed droplet may continue on to a mixing module. A similar method may take place for droplets dispensed from sample reservoir 1304 utilizing capacitive sensing circuit C2.

Figure 14A:
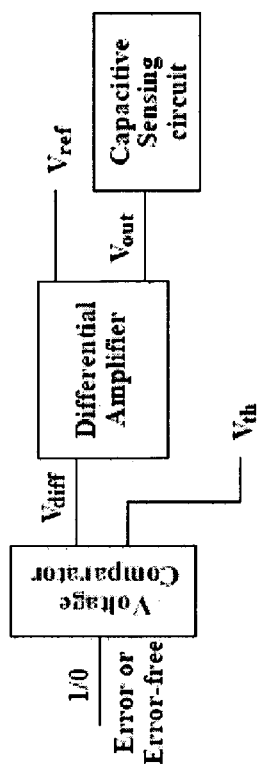
FIGS. 14A-B are example block diagrams of circuitry that may be associated with capacitive sensing electrodes.
Figure 14B:
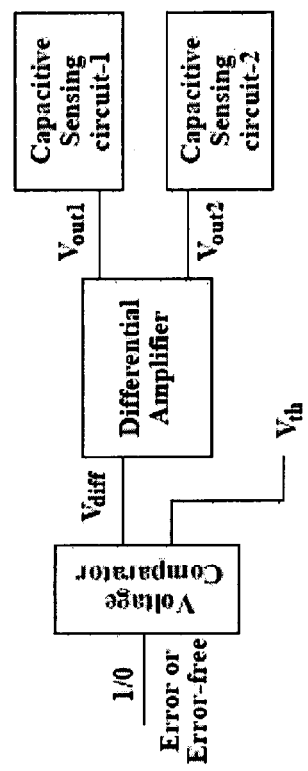

FIGS. 14A-14B are block diagrams illustrating circuitry that may be associated with capacitive sensing circuits. For example, the block diagram of FIG. 14A, may be used with a capacitive sensing circuit to detect the volumetric error of a dispensed droplet. A voltage comparator and differential amplifier may be used to identify the voltage difference between the voltage produced from a capacitive sensing circuit associated electrode and a reference voltage, $V_{ref}$. $V_{ref}$ may represent a calibrated average voltage of previously dispensed normal size test droplets of the same fluid. If the difference between $V_{ref}$ and the capacitive sensing circuit voltage is greater than a threshold value, $V_{th}$, then the output of the block diagram is a 1, indicating an unallowable volumetric error of the dispensed droplet of the fluid. $V_{th}$ may represent a maximum allowable error (e.g., 7% of $V_{ref}$, depending on the application requirement). If the difference is less than $V_{th}$, then the output of the block diagram is a 0, indicating an allowable volumetric error of the dispensed droplet of the fluid.

The block diagram of FIG. 14B may be associated with capacitive sensing circuits used to compare droplet volumes of the two split droplets of same fluid after a mix/split step. A voltage comparator and differential amplifier may be used to identify the voltage difference between the voltage output of a first capacitive sensing electrode and the voltage output of a second capacitive sensing electrode. If the difference between the two voltages is greater than a threshold value, $V_{th}$, then the output of the block diagram is a 1, indicating an unallowable error in the volume difference of the two split droplets. $V_{th}$ may represent a maximum allowable error (e.g., 7% of $V_{ref}$, depending on the application requirement). If the difference is less than $V_{th}$, then the output of the block diagram is a 0, indicating an allowable error in the volume difference of the two split droplets.

After splitting a resultant mixture into two unit-volume droplets, each droplet's volume may be compared using capacitive sensing circuits C3 and C4 (if the split step took place at MD or capacitive sensing circuits C3 and C5 (if the split step took place at M2). For example, after a mix and split step at M1, each resultant droplet may be transported to one of platforms C4 and C3. As described with reference to FIG. 14B, a differential amplifier is used to measure the difference in voltage readings (if any) corresponding to the capacitive sensing circuits C4 and C3 to compare the droplet volumes. If the difference between the readings is not within an allowable error threshold (e.g., 7% of some previously calibrated $V_{ref}$, depending on the application requirement), then the droplets may return to the mixing module M1 to be re-mixed and re-split. If after a threshold number of re-mixes and re-splits, the volume comparison still yields an unallowable difference in volumes of the two split droplets, then those droplets may be discarded and the sequence of mix steps may be rolled back using an available stored waste droplet or restarted from the beginning of the sequence. If a comparison yields an allowable difference in volumes of the two split droplets, then the sequence of mix steps may continue on. As described with reference to FIG. 14B, a voltage comparator may be used to compare the volumetric error with the error threshold value to decide upon whether there is an unallowable volumetric error or not.

Figure 15:
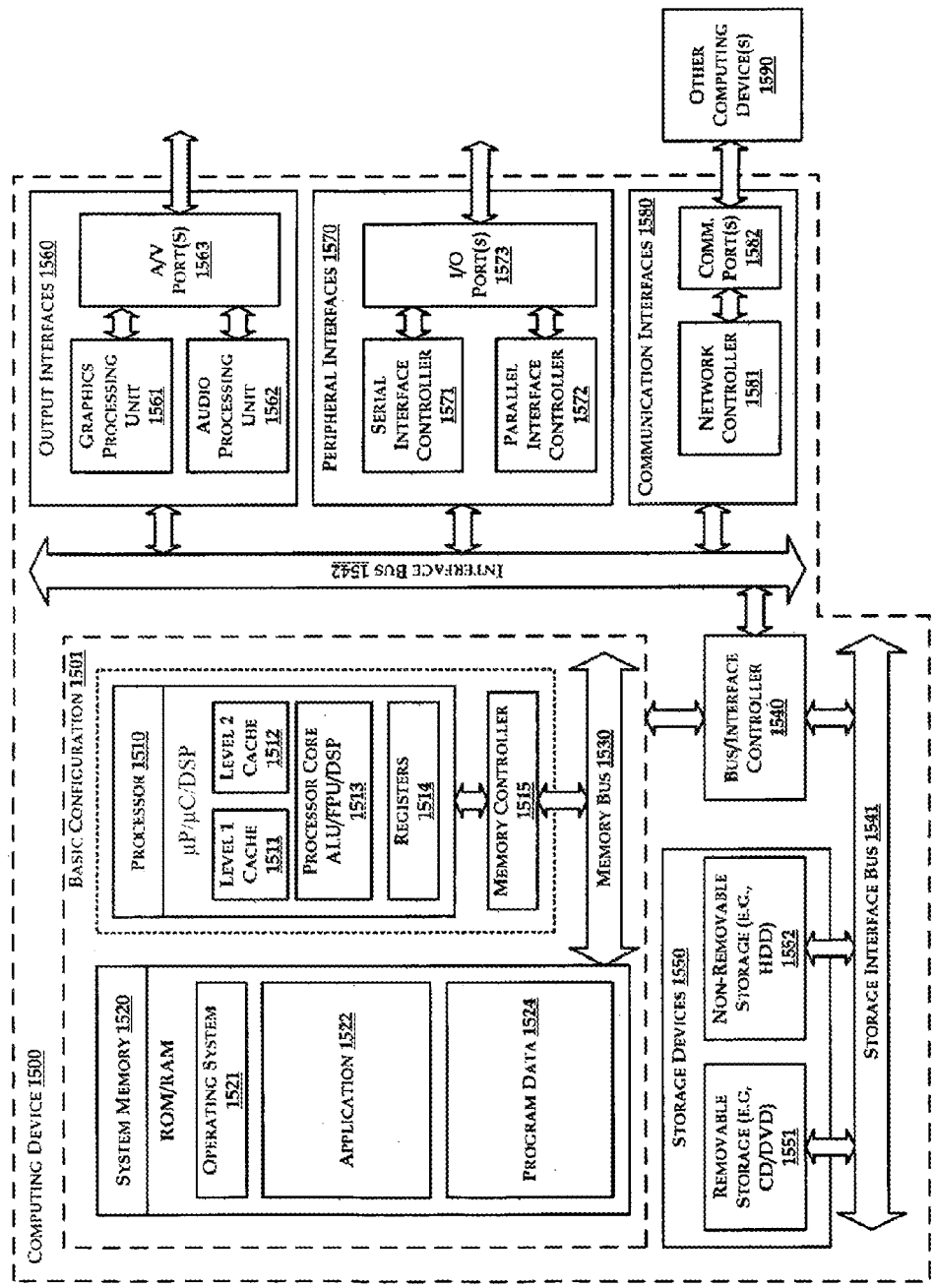
FIG. 15 is a block diagram illustrating an example computing device arranged for generating software instructions to carry out one or more methods described herein.

FIG. 15 is a block diagram illustrating an example computing device 1500 that may be associated with a biochip. All or part of computing device 1500 may be embedded within a biochip, or a biochip may be designed to couple with all or part of computing device 1500 outside of the biochip (e.g., to receive instructions).

In a very basic configuration 1501, computing device 1500 typically includes one or more processors 1510 and system memory 1520. A memory bus 1530 can be used for communicating between the processor 1510 and the system memory 1520.

Depending on the desired configuration, processor 1510 can be of any type including but not limited to a microprocessor (µP), a microcontroller (µC), a digital signal processor (DSP), or any combination thereof. Processor 1510 can include one more levels of caching, such as a level one cache 1511 and a level two cache 1512, a processor core 1513, and registers 1514. The processor core 1513 can include an arithmetic logic unit (ALU), a floating point unit (FPU), a digital signal processing core (DSP Core), or any combination thereof. A memory controller 1515 can also be used with the processor 1510, or in some implementations the memory controller 1515 can be an internal part of the processor 1510.

Depending on the desired configuration, the system memory 1520 can be of any type including but not limited to volatile memory (such as RAM), non-volatile memory (such as ROM, flash memory, etc.) or any combination thereof. System memory 1520 typically includes an operating system 1521, one or more applications 1522, and program data 1524.

Application 1522 may include all or part of the disclosed algorithms. For example, application 1522 may receive as an input the desired target concentration factor, the concentration factors of the initial reagent and buffer solutions, and the desired number of target CF droplets. The application 1522 may responsively determine the appropriate mix/split steps to achieve the desired target concentration factor. Further, application 1522 may determine instructions for carrying out the determined mix/split steps as well. For example, in a DMF-based biochip device associated with computing device 1500, these instructions may comprise appropriate actuation sequences for causing an array of DMF-based electrode platforms to carry out the determined mix/split steps. Such instructions may take the form of a bit pattern, for example.

In order to cause the DMF-based electrode platforms to carry out the determined sequence of mix steps, the appropriate actuation sequences may be fed to one or more peripheral interfaces. The I/O ports 1573 may be coupled to the platforms, and based on the received actuation sequences, apply voltages to the platforms such that the determined sequence of mix steps is carried out.

Computing device 1500 can have additional features or functionality, and additional interfaces to facilitate communications between the basic configuration 1501 and any required devices and interfaces. For example, a bus/interface controller 1540 can be used to facilitate communications between the basic configuration 1501 and one or more data storage devices 1550 via a storage interface bus 1541. The data storage devices 1550 can be removable storage devices 1551, non-removable storage devices 1552, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage of information, such as computer readable instructions, data structures, program modules, or other data.

System memory 1520, removable storage 1551 and non-removable storage 1552 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1500. Any such computer storage media can be part of device 1500.

Computing device 1500 can also include an interface bus 1542 for facilitating communication from various interface devices (e.g., output interfaces, peripheral interfaces, and communication interfaces) to the basic configuration 1501 via the bus/interface controller 1540. Example output interfaces 1560 include a graphics processing unit 1561 and an audio processing unit 1562, which can be configured to communicate to various external devices such as a display or speakers via one or more A/V ports 1563. Example peripheral interfaces 1570 include a serial interface controller 1571 or a parallel interface controller 1572, which can be configured to communicate with external devices such as input devices (e.g., keyboard, mouse, pen, voice input device, touch input device, etc.) or other peripheral devices (e.g., printer, scanner, etc.) via one or more I/O ports 1573. An example communication interface 1580 includes a network controller 1581, which can be arranged to facilitate communications with one or more other computing devices 1590 over a network communication via one or more communication ports 1582. The Communication connection is one example of a communication media. Communication media may typically be embodied by computer readable instructions, data structures, program modules, or other data in a modulated data signal, such as a carrier wave or other transport mechanism, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media. The term computer readable media (or medium) as used herein can include both storage media and communication media.

Computing device 1500 can be implemented as a portion of a microfluidic biochip. Computing device 1500 can also be implemented as a personal computer including both laptop computer and non-laptop computer configurations.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions, or materials, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed:

1. A method for producing a number (M) of diluted fluid droplets having a target concentration factor (CF) on a digital microfluidic (DMF) biochip, the method comprising:
    performing a sequence of mixing steps;
    during the sequence of mixing steps:
        transporting a first droplet to a first capacitive sensing circuit associated electrode;
        calculating a difference between (i) a first reading resulting from the first capacitive sensing circuit associated electrode holding the first droplet and (ii) a reference value; and
        when the difference between the first reading and the reference value is smaller than a threshold difference, continuing with the sequence of mix steps.

2. The method of claim 1, wherein the first droplet is transported from a sample reservoir, and wherein the method further comprises when the difference between the first reading and the reference value is smaller than a threshold difference, transporting the droplet from the first capacitive sensing circuit associated electrode to a mixing module.

3. The method of claim 2, further comprising calibrating the first capacitive sensing circuit associated electrode by averaging voltage values produced from two or more iterations of transporting a droplet to the first capacitive sensing circuit associated electrode from the sample reservoir, wherein the reference value is the average of the voltage values.

4. The method of claim 1, further comprising:
    transporting a second droplet to a second capacitive sensing circuit associated electrode, wherein the reference value is a second reading resulting from the second capacitive sensing circuit associated electrode holding the second droplet, and wherein the first and second droplets were split from a resultant mixture produced in one of the sequence of mix steps.

5. The method of claim 4, further comprising responsive to determining that the calculated difference is greater than a threshold difference, taking an action from the group consisting of (i) re-mixing the two resultant droplets, and (ii) discarding the two resultant droplets and mixing together two additional droplets to produce an additional resultant mixture having a concentration factor (CF) substantially equal to a CF of the resultant mixture.

6. The method of claim 5, wherein the threshold difference is a threshold error level for the difference between the readings produced from the first and second capacitive sensing circuit associated electrodes.

7. The method of claim 4, wherein a voltage comparator circuit is configured to calculate the difference between the first and second readings.

8. The method of claim 7, wherein the first reading is a voltage value and is based on a volume and concentration factor (CF) of a droplet held on the first capacitive sensing circuit associated electrode.

9. The method of claim 1, the biochip comprising a plurality of DMF-based electrode platforms arranged to carry out a sequence of mixing and splitting steps, the method further comprising:
    determining a target CF for an end resultant fluid mixture;
    expressing the target CF as an N-bit binary fraction;
    wherein each given mixing step of the sequence of mixing steps comprises:
        mixing together two input sample fluid droplets having different CFs to produce a first resultant mixture having a given resultant CF;
        splitting the first resultant mixture into a first resultant droplet and a second resultant droplet;
        using the N-bit binary fraction at least partially as a basis for determining which of the two input sample fluids will be mixed with the first resultant droplet;
        wherein when the N-bit binary fraction is a first binary value indicating that the resultant mixture produced in the given mixing step has a resultant CF larger than the target CF, mixing the first resultant droplet with a droplet of a first one of two input sample fluids in the next mixing step of the sequence of mixing steps;
        wherein when the N-bit binary fraction is a second binary value indicating that the resultant mixture produced in the given mixing step has a resultant CF smaller than the target CF, mixing the first resultant droplet with a droplet of a second one of two input sample fluids that is different from the first input sample in the next mixing step of the sequence of mixing steps;
    determining a desired amount of droplets of the end resultant fluid mixture; and
    performing one or more additional mixing steps comprising mixing a droplet of one of the two input sample fluids with the second resultant droplet split from the resultant mixture at least partially based on the N-bit binary fraction of the second resultant droplet, the one or more additional mixing steps producing a given second resultant mixture having a CF substantially equal to the target CF of the end resultant mixture, wherein the amount of the second resultant mixture and the number of the one or more additional mixing steps are at least partially based on the desired amount of droplets of the end resultant fluid mixture.

10. The method of claim 9, wherein one or more mixing steps of the sequence of mixing steps each further comprises transporting the second resultant droplet to one of a plurality of storage platforms; and
    wherein the one or more additional mixing step comprising mixing a droplet of one of the two input sample fluids with a second resultant droplet split from a resultant mixture produced in one of the sequence of mixing steps comprises:

at least one additional mixing step comprising:
- (a) transporting a second resultant droplet produced in one of the one or more mixing steps from one of the plurality of storage platforms to a mixing module,
- (b) transporting a sample droplet of one of the two sample fluids to the mixing module, and
- (c) mixing at the mixing module the transported resultant droplet and the transported sample droplet producing a given resultant mixture having a CF substantially equal to a CF of a resultant mixture produced in one of the one or more subsequent mixing steps.

11. The method of claim 10, wherein the one or more mixing steps of the sequence of mixing steps are sequential and begin with a $j^{th}$-to-last mixing step, where j is expressed as:

$$j = \lceil \log_2 M \rceil.$$

where $M < 2^N$, and
wherein (a) transporting a second resultant droplet produced in one of the one or more mixing steps from one of the plurality of storage platforms to a mixing module comprises:
of a plurality of second resultant droplets produced in one of the one or more mixing steps and stored on the plurality of storage platforms, transporting a second resultant droplet that was produced in a most recent mixing step from one of the plurality of storage platforms to the mixing module.

12. The method of claim 11, further comprising discarding each second resultant droplet produced in a first through $(j-1)^{th}$ mixing steps of the sequence of mixing steps.

13. The method of claim 10, wherein at least one of the sequence of mixing steps takes place at the mixing module, and wherein at least one of the sequence of mixing steps takes place at a second mixing module.

14. The method of claim 13, wherein one of the one or more subsequent mixing steps and the one or more one additional mixing step takes place about simultaneously and at different mixing modules.

15. The method of claim 14, wherein at least one of the one or more subsequent mixing steps take place at a first mixing module on the DMF biochip, and wherein the one or more one additional mixing step takes place at a second mixing module.

16. The method of claim 14, wherein the target CF is expressed as $$\frac{T}{2^N},$$

and wherein when the number of mixing steps in the sequence of mixing steps is equal to N, then (i) a given CF is substantially equal to the target CF when the given CF is equal to the target $$CF \pm \frac{1}{2^N},$$

and (ii) a given CF is not substantially equal to the target CF when the given CF is not equal to the target $$CF \pm \frac{1}{2^N}.$$

17. A non-transitory computer readable medium having computer executable instructions stored thereon, which when executed by a computing device, causes the computing device to carry out a sequence of operations, the operations comprising:
- determining a target concentration factor (CF) for a end resultant fluid mixture;
- expressing the target CF as an N-bit binary fraction;
- determining a sequence of mixing steps, which when carried out, produces two target droplets having the target (CF), wherein each given mixing step of the sequence of mixing steps comprises
- mixing two input sample fluid droplets having different CFs together to produce a first resultant mixture having a resultant CF;
- splitting the first resultant mixture into a first resultant droplet and a second resultant droplet;
- using the N-bit binary fraction at least partially as a basis for determining which of the two input sample fluids will be mixed with the first resultant droplet;
  - wherein when the N-bit binary fraction is a first binary value indicating that the resultant mixture produced in the given mixing step has a resultant CF larger than the target CF, mixing the first resultant droplet with a droplet of a first one of two input sample fluids in the next mixing step of the sequence of mixing steps;
  - wherein when the N-bit binary fraction is a second binary value indicating that the resultant mixture produced in the given mixing step has a resultant CF smaller than the target CF, mixing the first resultant droplet with a droplet of a second one of two input sample fluids that is different from the first input sample in the next mixing step of the sequence of mixing steps;
- determining a desired amount of droplets of the end resultant fluid mixture; and
- performing one or more additional mixing steps comprising mixing a droplet of one of the two input sample fluids with the second resultant droplet split from the resultant mixture at least partially based on the N-bit binary fraction of the second resultant droplet, the one or more additional mixing steps producing a given second resultant mixture having a CF substantially equal to the target CF of the end resultant mixture, wherein the amount of the second resultant mixture and the number of the one or more additional mixing steps are at least partially based on the desired amount of droplets of the end resultant fluid mixture.

18. The computer readable medium of claim 17, wherein the sequence of operations further comprises:
determining that a $j^{th}$-to-last mixing step of the sequence of mixing steps is a mixing step at which to begin storing the produced second resultant droplets so as to use the produced second resultant droplets in the one or more additional mixing steps to produce an additional two or more target droplets, wherein j is expressed as:

$$j = \lceil \log_2 M \rceil.$$

wherein $M<2^N$, and wherein N is an integer value, and wherein the number of mixing steps in the sequence of mixing steps is less than or equal to N.

19. The computer readable medium of claim 18, wherein the sequence of operations further comprises:

determining that each second resultant droplet produced in each mixing step before the $j^{th}$-to-last mixing step of the sequence of mixing steps should be discarded.

20. The computer readable medium of claim 17, wherein the two input sample fluids have respective CFs expressed as:

$$\frac{L}{2^N} \text{ and } \frac{H}{2^N},$$

and wherein the target CF is expressed as:

$$\frac{T}{2^N},$$

and wherein at least one of the two sample fluids has a CF that is both greater than 0% and less than 100%, and wherein expressing the target CF as the N-bit binary fraction comprises:

transforming the target CF into a transformed target CF expressed as:

$$\frac{T - L/H - L}{2^N};$$

and expressing the transformed target CF as an N-bit binary fraction, whereby the N-bit binary fraction is used as the basis for determining which of the two sample fluids will be mixed in a next mixing step with the first resultant droplet split in each given mixing step of the sequence of mixing steps.

21. The computer readable medium of claim 20, wherein the sequence of operations further comprises determining an appropriate sequence of voltages, which when applied to an arrangement of digital microfluidic (DMF)-based electrode platforms, cause the arrangement of electrode platforms to carry out the determined sequence of mixing steps.

* * * * *

UNITED STATES PATENT AND TRADEMARK OFFICE
CERTIFICATE OF CORRECTION

PATENT NO. : 9,128,014 B2  
APPLICATION NO. : 13/809328  
DATED : September 8, 2015  
INVENTOR(S) : Bhattacharya et al.

Page 1 of 1

It is certified that error appears in the above-identified patent and that said Letters Patent is hereby corrected as shown below:

In the Specification

In Column 1, Line 10, delete "§371" and insert -- § 371 --, therefor.

In Column 1, Line 12, delete "§119(d)" and insert -- § 119(d) --, therefor.

In Column 4, Line 41, delete "1-2 mL," and insert -- 1-2 nL, --, therefor.

In Column 6, Line 15, delete "$C_L < C_T < C_H$)." and insert -- $C_L \leq C_T \leq C_H$). --, therefor.

In Column 13, Line 37, delete "as in" and insert -- as 'b' in --, therefor.

In Column 14, Line 19, delete "2" target" and insert -- $2^n$ target --, therefor.

In Column 16, Line 44, delete "where '∈' is" and insert -- where 'ε' is --, therefor.

In Column 16, Line 46, delete "and is the" and insert -- and 'd' is the --, therefor.

In Column 17, Line 50, delete "MD or" and insert -- M1) or --, therefor.

In the Claims

In Column 23, Line 20, in Claim 11, "$j = \lceil \log_2 M \rceil$." and insert -- $j = \lceil \log_2 M \rceil$, --, therefor.

Signed and Sealed this  
Tenth Day of May, 2016

Michelle K. Lee  
*Director of the United States Patent and Trademark Office*